United States Patent
Kunio

(10) Patent No.: US 11,324,468 B2
(45) Date of Patent: May 10, 2022

(54) METHOD FOR CO-REGISTERING AND DISPLAYING MULTIPLE IMAGING MODALITIES

(71) Applicant: CANON U.S.A., INC., Melville, NY (US)

(72) Inventor: Mie Kunio, Boston, MA (US)

(73) Assignee: Canon U.S.A., Inc., Melville, NY (US)

(*) Notice: Subject to any disclaimer, the term of this patent is extended or adjusted under 35 U.S.C. 154(b) by 28 days.

(21) Appl. No.: 16/863,420

(22) Filed: Apr. 30, 2020

(65) Prior Publication Data

US 2020/0253575 A1  Aug. 13, 2020

Related U.S. Application Data

(63) Continuation of application No. 16/044,881, filed on Jul. 25, 2018, now Pat. No. 10,674,985.

(Continued)

(51) Int. Cl.
*G06K 9/00* (2022.01)
*A61B 6/00* (2006.01)
(Continued)

(52) U.S. Cl.
CPC ............ *A61B 6/5211* (2013.01); *A61B 6/504* (2013.01); *A61B 90/39* (2016.02); *G06K 9/342* (2013.01);
(Continued)

(58) Field of Classification Search
CPC ....... A61B 6/5211; A61B 90/39; A61B 6/504; A61B 2090/3782; A61B 2090/376;
(Continued)

(56) References Cited

U.S. PATENT DOCUMENTS 5,357,550 A   10/1994  Asahina et al.
6,763,261 B2  7/2004  Casscells, III et al.
(Continued)

FOREIGN PATENT DOCUMENTS

JP   2010-526556 A   8/2010
JP   2013-000583 A   1/2013
(Continued)

OTHER PUBLICATIONS

Andreas et al, ("Geometrically Correct 3-D Reconstruction of Intravascular Ultrasound Images by Fusion with Biplane Angiography—Methods and Validation", IEEE Transaction on medical Imaging, vol. 18, No. 8, Aug. 1999). (Year: 1999).*

(Continued)

*Primary Examiner* — Amara Abdi
(74) *Attorney, Agent, or Firm* — Canon U.S.A., Inc. I.P. Division

(57) ABSTRACT

A method for processing angiography image data by using an imaging catheter path that is directly detected from the angiography data as a co-registration path or using detected marker locations from the angiography data to generate a co-registration path. If the acquired angiography data includes synchronized cardiac phase signals and a predetermined quantity of angiography image frames not including contrast media, then a directly detected imaging catheter path is used as the co-registration path. Otherwise the co-registration path is determined based upon detected marker locations from the angiography image data.

17 Claims, 18 Drawing Sheets

Related U.S. Application Data

(60) Provisional application No. 62/680,780, filed on Jun. 5, 2018, provisional application No. 62/537,204, filed on Jul. 26, 2017.

(51) Int. Cl.

| | | |
|---|---|---|
| *G06T 7/30* | (2017.01) | |
| *G06T 7/20* | (2017.01) | |
| *A61B 90/00* | (2016.01) | |
| *G06T 7/12* | (2017.01) | |
| *G06K 9/34* | (2006.01) | |
| *G06K 9/46* | (2006.01) | |
| *G06T 7/00* | (2017.01) | |
| *G06T 7/181* | (2017.01) | |
| *G06T 7/11* | (2017.01) | |
| *G06K 9/44* | (2006.01) | |

(52) U.S. Cl.
CPC .......... *G06K 9/4638* (2013.01); *G06T 7/0012* (2013.01); *G06T 7/12* (2017.01); *G06T 7/20* (2013.01); *G06T 7/30* (2017.01); *A61B 6/4441* (2013.01); *A61B 2090/363* (2016.02); *A61B 2090/3614* (2016.02); *A61B 2090/376* (2016.02); *A61B 2090/3735* (2016.02); *A61B 2090/3782* (2016.02); *A61B 2090/3966* (2016.02); *G06K 9/44* (2013.01); *G06K 2009/00932* (2013.01); *G06K 2209/05* (2013.01); *G06T 7/11* (2017.01); *G06T 7/181* (2017.01); *G06T 2207/10081* (2013.01); *G06T 2207/10116* (2013.01); *G06T 2207/20092* (2013.01); *G06T 2207/30101* (2013.01)

(58) Field of Classification Search
CPC ...... A61B 2090/3735; A61B 2090/363; A61B 2090/3614; A61B 6/4441; A61B 2090/3966; A61B 6/486; A61B 6/503; A61B 6/5264; A61B 2090/364; A61B 5/0035; A61B 5/0066; A61B 5/0084; A61B 5/02007; A61B 6/00; A61B 6/12; A61B 6/481; A61B 6/487; A61B 6/5247; A61B 8/0891; A61B 8/12; A61B 8/5238; A61B 90/37; G06T 7/12; G06T 7/0012; G06T 7/30; G06T 7/20; G06T 7/181; G06T 7/11; G06T 2207/10081; G06T 2207/10116; G06T 2207/20092; G06T 2207/30101; G06T 7/33; G06T 2200/24; G06T 2207/10016; G06T 2207/10101; G06T 2207/10121; G06T 2207/10132; G06T 2207/20044; G06T 2207/20101; G06T 2207/30021; G06T 2207/30172; G06T 2207/30204; G06T 2211/404; G06T 7/0016; G06T 7/251; G06T 7/337; G06K 9/342; G06K 9/4638; G06K 9/44; G06K 2009/00932; G06K 2209/05; G01N 2800/323; G16H 50/20

See application file for complete search history.

(56) References Cited

U.S. PATENT DOCUMENTS

| | | | |
|---|---|---|---|
| 7,978,916 B2 | 7/2011 | Klingensmith et al. | |
| 8,175,684 B2 | 5/2012 | Vaillant et al. | |
| 8,478,387 B2 | 7/2013 | Xu | |
| 8,565,859 B2 | 10/2013 | Wang et al. | |
| 8,909,323 B2 | 12/2014 | Baumgart | |
| RE45,534 E | 6/2015 | Huennekens et al. | |
| 9,121,926 B2* | 9/2015 | Nair | A61B 8/463 |
| 9,138,147 B2 | 9/2015 | Schmitt et al. | |
| 9,286,673 B2 | 3/2016 | Begin et al. | |
| 9,292,918 B2 | 3/2016 | Zagrodsky et al. | |
| 9,295,450 B2 | 3/2016 | Furuichi et al. | |
| 9,301,687 B2 | 4/2016 | Kemp | |
| 9,307,926 B2 | 4/2016 | Begin et al. | |
| 9,351,698 B2* | 5/2016 | Dascal | G06T 7/11 |
| 9,462,950 B2 | 10/2016 | Xu | |
| 9,833,221 B2 | 12/2017 | Hutchins et al. | |
| 9,855,384 B2 | 1/2018 | Cohen et al. | |
| 9,901,317 B2 | 2/2018 | Shimamura et al. | |
| 2008/0091171 A1* | 4/2008 | Strommer | A61B 6/12 604/528 |
| 2010/0208957 A1 | 8/2010 | Chen et al. | |
| 2011/0230758 A1 | 9/2011 | Eichler | |
| 2014/0176961 A1* | 6/2014 | Johansson | A61B 5/0073 356/479 |
| 2014/0270436 A1* | 9/2014 | Dascal | A61B 6/463 382/130 |
| 2014/0276011 A1 | 9/2014 | Schmitt et al. | |
| 2015/0131886 A1* | 5/2015 | Aben | A61B 8/5261 382/132 |
| 2015/0250438 A1* | 9/2015 | Bozkaya | A61B 5/026 600/424 |
| 2015/0272442 A1 | 10/2015 | Motafakker-Fard et al. | |
| 2016/0099010 A1* | 4/2016 | Sainath | G06N 3/0445 704/232 |
| 2016/0171711 A1 | 6/2016 | Gopinath et al. | |
| 2016/0196666 A1* | 7/2016 | Venkatraghavan | G06T 7/248 382/130 |
| 2016/0206267 A1* | 7/2016 | Shimizu | A61B 1/3137 |
| 2016/0335766 A1* | 11/2016 | Ambwani | G06K 9/4647 |
| 2017/0020392 A1 | 1/2017 | Xu | |
| 2017/0024532 A1 | 1/2017 | Gopinath et al. | |
| 2017/0135663 A1* | 5/2017 | Dascal | G06T 5/50 |

FOREIGN PATENT DOCUMENTS

| | | |
|---|---|---|
| JP | 2013-56113 A | 3/2013 |
| JP | 2015-093131 A | 5/2015 |
| JP | 2015-109968 A | 6/2015 |
| WO | 2008/013255 A1 | 1/2008 |
| WO | 2014/175853 A1 | 10/2014 |
| WO | 2015/044979 A1 | 4/2015 |
| WO | 2015/045368 A1 | 4/2015 |

OTHER PUBLICATIONS

Athanasiou, L.S., et al., "3D Reconstruction of Coronay Arteries using Frequency Domain Optical Coherence Tomography Images and Biplane Angiography", IEEE, Aug. 2012 (four pages).

Blondel, C., et al., "Reconstruction of Coronary Arteries From a Single Rotational X-Ray Projection Sequence", IEEE Transactions on Medical Imaging, vol. 25, No. 5, May 2006, pp. 653-663.

Bourantas, C. V., et al., "A new methodology for accurate 3-dimensional coronary artery reconstruction using routine intravascular ultrasound and angiographic data: implications for widespread assessment of endothelial shear stress in humans", Euro Intervention, vol. 9, Apr. 2013, pp. 582-593.

Bourantas, C. V., et al., "Angiocare: An Automated System for Fast Three-Dimesional Coronary Reconstruction by Integrating Angiographic and Intracoronay Ultrasound Data", Catheterization and Cardiovascular Intervention, vol. 72, Apr. 2008, pp. 166-175.

Bourantas, C. V., et al., "Bioresorbable vascular scaffold treatment induces the formation of neointimal cap that seals the underlying plaque without compromising the luminal dimensions: a concept based on serial optical coherence tomography data", Euro Intervention, Oct. 2014, pp. 1-16.

Bourantas, C.V., et al., "A method for 3D reconstruction of coronary arteries using biplane angiography and intravascular ultrasound images", Computerized Medical Imaging and Graphics, vol. 29, Nov. 2005, pp. 597-606.

Cardenes, R., et al., "3D Reconstruction of Coronary Arteries From Rotational X-Ray Angiography", IEEE, May 2012, pp. 618-621.

Coskun, A. U., et al., "Reproducibility of Coronary Lumen, Plaque, and Vessel Wall Reconstruction and of Endothelial Shear Stress

(56) References Cited

OTHER PUBLICATIONS

Measurements In Vivo in Humans", Catheterization and Cardiovascular Interventions, vol. 60, Sep. 2003, pp. 67-78.

Dehkordi, et al., "Extraction of the Best Frames in Coronary Angiograms for Diagnosis and Analysis", J Med Signals, Sens. Jul.-Sep. 2016, vol. 6, No. 3, pp. 150-157.

Ellwein, L.M., et al.. Optical Coherence Tomography for Patient-specific 3D Artery Reconstruction and Evaluation of Wall Shear Stress in a Left Circumflex Coronary Artery, Cardiovascular Engineering and Technology, vol. 2, No. 3, Sep. 2011, pp. 212-227.

Giannoglou, G. D., et al., "In-vivo validation of spatially correct three-dimensional reconstruction of human coronary arteries by integrating intravascular ultrasound and biplane angiography", Diagnostic methods, vol. 17, No. 6, Sep. 2006, pp. 533-543.

Hebsgaard, L., et al., "Co-registration of optical coherence tomography and X-ray angiography in percutaneous coronary intervention. The Does Optical Coherence Tomography Optimize Revascularization (DOCTOR) fusion study", International Journal of Cardiology, vol. 182, Mar. 2015, pp. 272-278.

Hoffmann, K. R., et al., "Biplane X-ray angiograms, intravascular ultrasound, and 3D visualization of coronary vessels", International Journal of Cardiac Imaging, vol. 15, Dec. 1999, pp. 495-512.

Horsley, E., "Imaging for the Future . . . Intravascular Optical Coherence Tomography", Sep. 10, 2016; from https://www.slideshare.net/ErnestHorsley/coronary-optical-coherence-tomography-oct-angio-coregistration-acr-and-metal-stent-optimisation-mso-softwarefrom.

Kang, D., et al., "Three-Dimensional Blood Vessel Quantification via Centerline Deformation", IEEE Transactions on Medical Imaging, vol. 28, No. 3, Mar. 2009, pp. 405-414.

Khaleel, H. H., et al., "A Review paper of 3D Surface Reconstruction of Coronary Arteries From Cardiovascular Angiography", 2012 International Conference on Advanced Computer Science Applications and Technologies (Acsat), pp. 419-435, Nov. 2012, DOI: Doi 10.1109/Acsat.2012.13.

Klein, H. M., et al., "3D-Surface Reconstruction of Intravascular Ultrasound Images Using Personal Computer Hardware and a Motorized Catheter Control", Cardiovascular Interventional Radiology, vol. 15, Mar.-Apr. 1992, pp. 97-101.

Kraus, M.F., et al., "Motion correction in optical coherence tomography volumes on a per A-scan basis using orthogonal scan patterns", Bio. Med. Express, vol. 3, No. 6, Jun. 1, 2012, pp. 1182-1199.

Kumar, R.P., et al., "3D multiscale vessel enhancement based centerline extraction of blood vessels", Medical Imaging 2013: Image Processing, Proc. SPIE vol. 8669, Mar. 2013 (ten pages).

Laban, M., et al., "ANGUS: A New Approach to Three-Dimensional Reconstruction of Coronary Vessels by Combined Use of Angiography and Intravascular Ultrasound", Computers in Cardiology, IEEE, Oct. 1995, pp. 325-238.

Li, Y., et al., "Impact of Side Branch Modeling on Computation of Endothelial Shear Stress in Coronary Artery Disease: Coronary Tree Reconstruction by Fusion of 3D Angiography and OCT", Journal of the American College of Cardiology, vol. 66, Issue No. 2, Jul. 2015, pp. 125-135.

Maehara, et al., "Assessment and Quantification of Stent Results by Intracoronary Optical Coherence Tomography", Intervent. Cardiol. Clin., vol. 4, Issue 3, Jul. 2015, pp. 285-294.

Oubel, et al., "Analysis of Intracranial Aneurysm Wall Motion and its Effects on Hemodynamic Patterns", Proc. SPIE, Medical Imaging, vol. 6511, Mar. 2007 (eight pages included).

Peng Wang, et al., "Image-based Co-Registration of Angiography and Intravascular Ultrasound Images", IEEE Transactions on Medical Imaging, vol. 32, No. 12, Dec. 2013, pp. 2238-2249.

Prati, et al., "Clinical Impact of OCT Findings During PCI: The CLI-OPCI II Study", JACC: Cardiovascular Imaging, vol. 8, No. 11, Nov. 2015, pp. 1297-1305.

Reiber, J., et al., "QCA, IVUS and OCT in interventional cardiology in 2011", Cardiovascular Diagnosis and Therapy, vol. 1, No. 1, Dec. 2011, pp. 57-70.

Rivest-Hénault, D., et al., "Nonrigid 2D/3D Registration of Coronary Artery Models With Live Fluoroscopy for Guidance of Cardiac Interventions", IEEE Transations on Medical Imaging, vol. 31, No. 8, Aug. 2012, pp. 1557-1572.

Sarwal, A., et al., "Three dimensional reconstruction of coronary arteries from two views", Computer Methods and Programs in Biomedicine, vol. 65, Issue 1, Jan. 2001, pp. 25-43, ISSN: 0169-2607.

Shekhar, R., et al., "Fusion of Intravascular Ultrasound and Biplane Angiography for Three-Dimensional Reconstruction of Coronary Arteries", IEEE, Computers in Cardiology, Sep. 1996, pp. 5-8.

Slager, C. J., et al., "True 3-Dimensional Reconstruction of Coronary Arteries in Patients by Fusion of Angiography and IVUS (ANGUS) and Its Quantitative Validation", vol. 102, No. 5, Aug. 2000, pp. 511-516.

St Jude Web Page, "OPTIS Stent Optimization Software", Last updated Feb. 10, 2017: https://www.sjmglobal.com/professionals/resources-and-reimbursement/technical-resources/vascular/intravascular-diagnostics-and-imaging/intravascular-diagnostics-and-imaging-system-ffr-oct/optis-metallic-stent-optimization-software?halert=show&clset=92f57278-460e-4300-b7fe-89e52a04194f%3acadddb93-fcc4-47f2-8ceb-fd88f01ca17f (three pages included).

Subramanian, K. R., et al., "Accurate 3D reconstruction of complex blood vessel geometries from intravascular ultrasound images: in vitro study", Journal of Medical Engineering & Technology, vol. 24, No. 4, Jul./Aug. 2000, pp. 131-140.

Timmins, L. H., et al., "Framework to Co-register Longitudinal Virtual Histology—Intravascular Ultrasound Data in the Circumferential Direction", IEEE Transactions on Medical Imaging, vol. 32, No. 11, Nov. 2013, pp. 1989-1996.

Tu, S., et al., "Fusion of 3D QCA and IVUS/OCT", International Journal of Cardiovascular Imaging, vol. 27, Issue 2, Feb. 2011, pp. 197-207.

Tu, S., et al., "Assessment of obstruction length and optimal viewing angle from biplane X-ray angiograms", Int. J. Cardiovasc. Imaging, vol. 26, No. 1, Jan. 2010, pp. 5-17.

Tu, S., et al., "In vivo comparison of arterial lumen dimensions assessed by co-registered three-dimensional (3D) quantitative coronary angiography, intravascular ultrasound and optical coherence tomography", Int. J. Cardiovasc. Imaging, vol. 28, No. 6, Aug. 2012, pp. 1315-1327.

Tu, S., et al., "In Vivo Flow Simulation at Coronary Bifurcation Reconstructed by Fusion of 3-Dimensional X-ray Angiography and Optical Coherence Tomography", Circ. Cardiovasc. Interv., vol. 6, No. 2, Apr. 2013, pp. e15-e17 (5 pages included).

Ughi, G.J. et al., "Clinical Characterization of Coronary Atherosclerosis With Dual-Modality OCT and Near-Infrared Autofluorescence Imaging", JACC: Cardiovascular Imaging, Nov. 2016 (In press), pp. 1-11.

Van Der Giessen, A., et al., "3D fusion of intravascular ultrasound and coronary computed tomography for in-vivo wall shear stress analysis: a feasibility study", Int. J. Cardiovasc. Imaging, vol. 26, No. 7, Oct. 2010, pp. 781-796.

Wahle, A., et al., "Fusion of Angiography and Intravascular Ultrasound in vivo: Establishing the Absolute 3-D Frame Orientation", IEEE Transactions on Biomedical Engineering, vol. 46, No. 10, Oct. 1999, pp. 1176-1180.

Wahle, A., et al., "Geometrically Correct 3-D Reconstruction of Intravascular Ultrasound Images by Fusion with Biplane Angiography—Methods and Validation", IEEE Transactions on Medical Imaging, vol. 18, No. 8, Aug. 1999, pp. 686-699.

Yang, J., et al., "Novel Approach for 3-D Reconstruction of Coronary Arteries from Two Uncalibrated Angiographic Images", IEEE Transactions on Image Processing, vol. 18, No. 7, Jul. 2009, pp. 1563-1572.

Zhang, W., et al., "3D Vessel Tree Reconstruction from Rotational C-arm Projections by Multi-view Stereo Reconstruction", APCMBE 2008: 7th Asian-Pacific Conference on Medical and Biological Engineering, IFMBE Proceedings, vol. 19, Jan. 2008, pp. 434-441, ISBN: 1680-0737.

International Search Report and Written Opinion for PCT/US2018/043756 and notification of transmittal of the ISR/WO, dated Nov. 20, 2018.

(56) References Cited

OTHER PUBLICATIONS

Invitation to Pay Additional Fees for PCT/US2018/043743, dated Dec. 11, 2018.
Notification of Transmittal of ISR/WO, and International Search Report and Written Opinion, for PCT/US2018/043743 and notification of transmittal of the ISR/WO, dated Feb. 5, 2019.

* cited by examiner

METHOD FOR CO-REGISTERING AND DISPLAYING MULTIPLE IMAGING MODALITIES

CROSS-REFERENCE TO RELATED APPLICATIONS

The present application is a continuation of U.S. patent application Ser. No. 16/044,881, filed on Jul. 25, 2018, which claims priority to U.S. Provisional Application Ser. No. 62/537,204, filed Jul. 26, 2017, and to U.S. Provisional Application Ser. No. 62/680,780, filed Jun. 5, 2018, which applications are hereby incorporated by reference herein in their entireties.

BACKGROUND

Field of the Disclosure

The present disclosure relates in general to processing angiography image data, and more particularly, to a method that uses an angiography image frame to display the imaging catheter path and calculate the reliability of co-registration between multiple imaging modalities.

Description of the Related Art

Coronary angiography imaging and intravascular imaging are important imaging modalities for percutaneous coronary intervention (PCI). A coronary angiography provides longitudinal silhouettes of coronary arteries. The longitudinal silhouettes of the coronary artery are displayed on a monitor to help an interventional cardiologist guide a catheter insertion to a targeted region. Using coronary angiography during a PCI procedure is preferred because it is easier to guide the catheter to a lesion than other types of imaging modalities.

Another imaging modality used in PCI is intravascular imaging which provides cross-sectional information of coronary arteries. Intravascular imaging may include intravascular ultrasound (IVUS) and optical coherence tomography (OCT) that provides more precise lesion information than a coronary angiography image. However, relying only on an intravascular imaging modality such as IVUS or OCT in a PCI procedure is difficult when guiding a catheter to a targeted region such a lesion to gain information about a lumen size, plaque morphology or implanted devices by way of example.

A system that enables physicians to connect between two different imaging modalities including for example both coronary angiography and intravascular imaging during PCI involves co-registration. Co-registration refers to the spatial alignment of a series of images. For example, co-registration may refer to the alignment of functional (intravascular imaging) and structural images (coronary angiography) of a PCI patient to map functional information into anatomical space. One benefit associated with co-registering angiography imaging with intravascular imaging includes determining where along the longitudinal silhouette of the coronary artery in an angiography image frame the intravascular image was acquired.

One type of co-registration requires generating a vessel centerline from angiography. The generated vessel centerline is displayed on the angiography image frame. The vessel centerline is a representative line of the vessel's longitudinal direction. The co-registration location appears as an artificial marker on the angiography image frame. The co-registration location is the location where the intravascular image frame is captured.

Another type of co-registration between angiography and intravascular imaging is performed via three-dimensional (3D) trajectory of an imaging catheter path. The 3D trajectory is created by two angiography views. A user places indicators along the catheter path in both angiography views. The two angiography views must be acquired before intravascular imaging pullback. In other words, this method of co-registration requires generating an imaging catheter path from angiography data that is acquired prior to intravascular imaging pullback with user inputs.

The co-registration between coronary angiography and intravascular imaging results in a co-registration path. The co-registration path may refer to a targeted region of a coronary artery of the patient during PCI. The imaging catheter path is an actual path and thus may result in a more accurate co-registration result than a vessel centerline. However, detecting an imaging catheter path as the co-registration path is difficult when contrast media fully occupies the targeted region where the intravascular image is acquired. Therefore, the angiography image frame that is acquired prior to intravascular imaging pullback may be used to detect an imaging catheter path to avoid contrast media fully occupying the targeted region. An issue associated with this is the assumption that the location of the imaging catheter does not change before and during intravascular imaging pullback. If the imaging catheter path is detected from the angiography image frame acquired prior to the intravascular imaging pullback, any change to the location of the imaging catheter during the intravascular imaging pullback affects the accuracy of the imaging catheter path.

Another method to improve the accuracy may be the usage of 3D reconstructed co-registration path. To reconstruct a 3D path, multiple views of angiography image frame are required, which requires acquiring the angiography image frames prior to the intravascular imaging pullback. A 3D reconstruction is more processor and time intensive compared to a two-dimensional (2D) reconstruction of the co-registration path.

Thus, there is a need in the art for a system and method for processing angiography image data based on an imaging catheter path that is not affected by a change to the location of the imaging catheter during intravascular imaging pullback as well as displaying a 2D reconstruction of the co-registration path based on the imaging catheter path.

SUMMARY

The present disclosure is directed to a method for processing angiography image data using either a directly detected imaging catheter path or detected radiopaque marker locations from angiography data. The method may include acquiring a plurality of intravascular image frames and determining an acquisition location of the intravascular image frames on an angiography image frame from the angiography data that includes the generated co-registration path. The method may conclude by displaying the angiography image frame with the generated co-registration path as well as an indicator on the co-registration path that is representative of the acquisition location of an intravascular image frame on a display. An advantage of the present disclosure includes using angiography data that is acquired simultaneously during intravascular imaging pullback so that the imaging catheter path may reflect any change in location of the imaging catheter during the intravascular imaging pullback. Another advantage includes generating a co-registration path based on a directly detected imaging catheter path in 2D as well as by reconstructing based on detected radiopaque marker locations of the angiography data.

One embodiment of the present disclosure is directed to a method for processing angiography image data, the method may initiate with importing angiography data including a plurality of angiography image frames. The angiography data may be synchronized with cardiac phase signals such that each angiography image frame includes an associated cardiac phase signal. The method may continue with a first detecting step for detecting an imaging catheter path for angiography image frames not including contrast media in a targeted area and saving the imaging catheter path with the associated cardiac phase signal for angiography image frames not including contrast media in the targeted area. A second detecting step for detecting a vessel contour and a marker for angiography image frames including contrast media in the targeted area and saving the vessel contour, the marker and the associated cardiac phase signal for the angiography image frames including contrast media in the targeted area. The method may proceed by selecting an angiography image frame from the angiography image frames including contrast media and selecting an angiography image frame from the angiography image frames not including contrast media having identical cardiac phase signals, overlaying the angiography image frame from the angiography image frames including contrast media with the angiography image frame from the angiography image frame not including contrast media to determine whether the detected imaging catheter path in the angiography image frame from the angiography image frames not including contrast media is located within the vessel contour of the angiography image frame from the angiography image frames including contrast media, and a determining step for determining whether the marker associated with the angiography image frame from the angiography image frames including contrast media is located on the imaging catheter path of the angiography image frame from the angiography image frames not including contrast media in response to a determination that the imaging catheter path of the angiography image frame from the angiography image frames not including contrast media is located within the vessel contour of the angiography image frame from the angiography image frames including contrast media.

In another embodiment of the present disclosure, a method for processing angiography image data is executed by a memory and a processor within an intravascular imaging system. The intravascular imaging system may be configured to receive angiography data from an angiography system as well as display co-registration results on a display directly or via a network.

In another embodiment of the present disclosure, a method for processing angiography image data is executed by a memory and a processor within an angiography system. The angiography system may be configured to receive intravascular imaging data from an intravascular imaging system as well as display co-registration results on a display directly or via a network.

In another embodiment of the present disclosure, an image processor separate from an angiography system and intravascular imaging system may be configured to receive both angiography data and intravascular imaging data to execute a method for processing angiography image data. The image processor may connect with the angiography system and the intravascular imaging system via a network. The image processor may also generate instructions for displaying a co-registration result on a display as well as an acquisition location of an intravascular image on the displayed co-registration path.

Another embodiment of the present disclosure relates to a non-transitory computer-readable medium encoded with a plurality of processor-executable instructions to perform a method for processing angiography image data using either a directly detected imaging catheter path or an imaging catheter path based upon detected radiopaque marker locations associated with angiography data.

Further features of the present disclosure will become apparent from the following description of exemplary embodiments with reference to the attached drawings.

DETAILED DESCRIPTION

The following description is of certain illustrative embodiments, although other embodiments may include alternatives, equivalents, and modifications. Additionally, the illustrative embodiments may include several novel features, and a particular feature may not be essential to practice the devices, systems, and methods described herein.

The present disclosure includes using an angiography image frame that is simultaneously acquired during intravascular imaging pullback and generates an imaging catheter path based on a directly detected location of a radiopaque marker of an imaging catheter. By using the directly detected location, the reliability of co-registration may be calculated. The present disclosure is directed to displaying on a graphical user interface (GUI) an angiography image frame with a co-registration path to show where an intravascular imaging pullback procedure was performed along with an indicator to show the location where the intravascular image frame was acquired. The co-registration path is generated based on the imaging catheter path from an angiography image frame that is acquired during the intravascular imaging pullback.

One method for co-registration may include a catheter with a radiopaque marker at the tip used for intravascular imaging. The processor finds the radiopaque marker on the angiography image frames by searching a darkest point/mark in the image frames. The co-registration location is determined by finding a point that is proximal to the detected marker location with the known distance between the marker and the optical lens for imaging along the longitudinal direction of the coronary artery. There are other ways of co-registration, and the present disclosure is not limited to this one particular example of co-registration.

Figure 1:
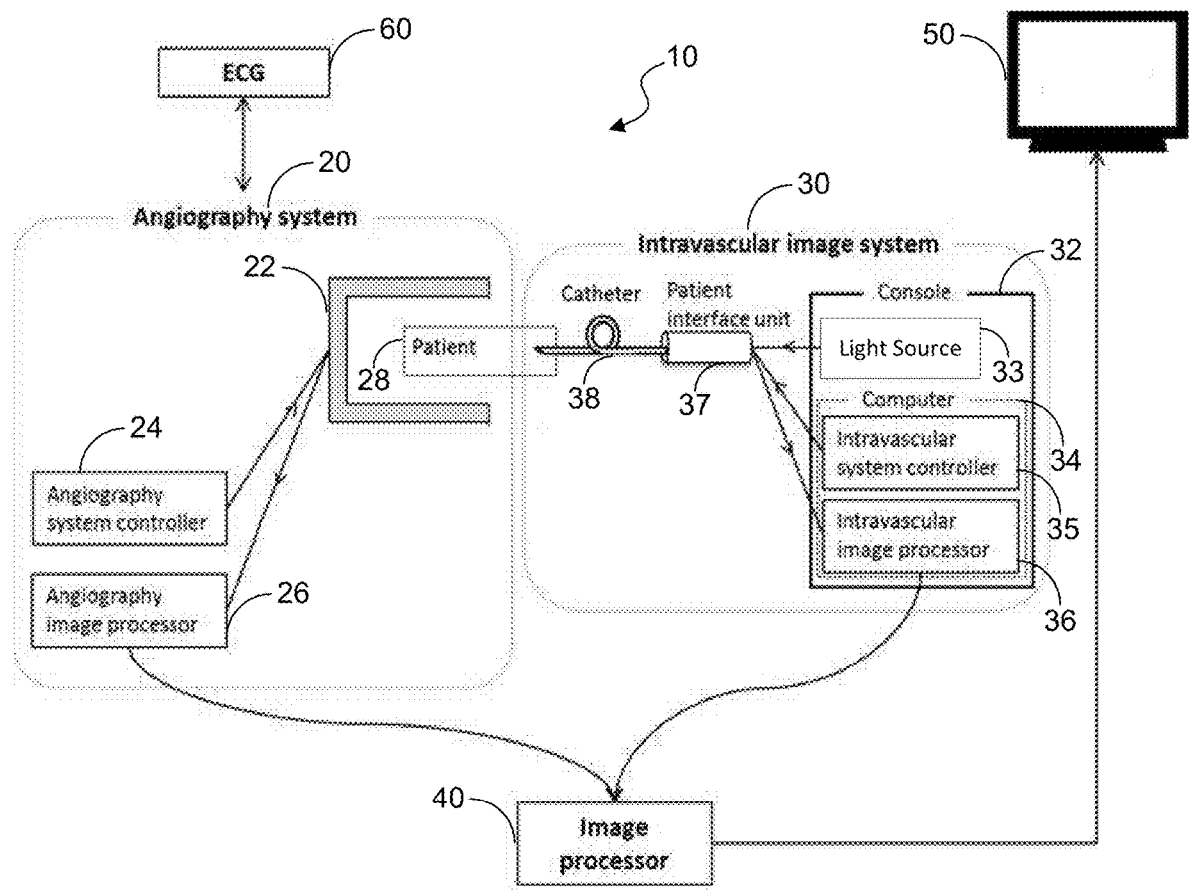
FIG. 1 is a schematic diagram illustrating an imaging system for executing various steps to process angiography image data in accordance with one or more aspects of the present disclosure.

Referring now to FIG. 1, shown is a schematic diagram of an exemplary imaging system 10 for generating an imaging catheter path based on either a directly detected location of a radiopaque marker on the imaging catheter or a regression line representing the imaging catheter path by using an angiography image frame that is simultaneously acquired during intravascular imaging pullback. The imaging system 10 includes an angiography system 20, an intravascular imaging system 30, an image processor 40, a display 50 and an electrocardiography (ECG) device 60. The angiography system 20 includes an X-ray imaging device such as a C-arm 22 that is connected to an angiography system controller 24 and an angiography image processor 26 for acquiring angiography image frames of a patient 28.

The intravascular imaging system 30 of the imaging system 10 includes a console 32, a catheter 38 and a patient interface unit 37 that connects between the catheter 38 and the console 32 for acquiring intravascular image frames. The catheter 38 is inserted into a blood vessel of the patient 28. The catheter 38 may function as a light irradiator and a data collection probe that is disposed in the lumen of a particular blood vessel, such as for example, a coronary artery. The catheter 38 typically includes a probe tip, one or more radiopaque markers, an optical fiber, and a torque wire. The probe tip may include one or more data collection systems. The catheter 38 is threaded in a patient's artery to obtain images of the coronary artery. The patient interface unit 37 has a motor inside to enable pullback of imaging optics during the acquisition of intravascular image frames. The imaging pullback procedure obtains images of the blood vessel. The imaging pullback path may represent the co-registration path which may be a region of interest or a targeted region of the vessel.

The console 32 includes a light source(s) 33 and a computer 34. The computer 34 includes an intravascular system controller 35 and an intravascular image processor 36. The intravascular image processor 35 controls the motor in the patient interface unit 37. The intravascular image processor 35 may also perform various steps for image processing and control the information to be displayed.

Various types of intravascular imaging systems may be used within the imaging system 10. The intravascular imaging system 30 is merely one example of an intravascular imaging system that may be used within the imaging system 10. Various types of intravascular imaging systems may be used including an OCT system, a multi-modality OCT system or an IVUS system by way of example.

The imaging system 10 may also include an electrocardiography (ECG) device 60 for recording the electrical activity of the heart over a period of time using electrodes placed on the skin of the patient 28. The imaging system 10 may also include an image processor 40 for receiving angiography data, intravascular imaging data and data from the ECG device 60 to execute various image processing steps to transmit to a display 50 for displaying an angiography image frame with a co-registration path. Although the image processor 40 associated with the imaging system 10 appears external to both the angiography system 20 and the intravascular imaging system 30, the image processor 40 may be included within the angiography system 20, the intravascular imaging system 30, the display 50 or a stand-alone device. Alternatively, the image processor 40 may not be required if the various image processing steps are executed using either the angiography image processor 26 or the intravascular image processor 36 of the imaging system 10.

Figure 2:
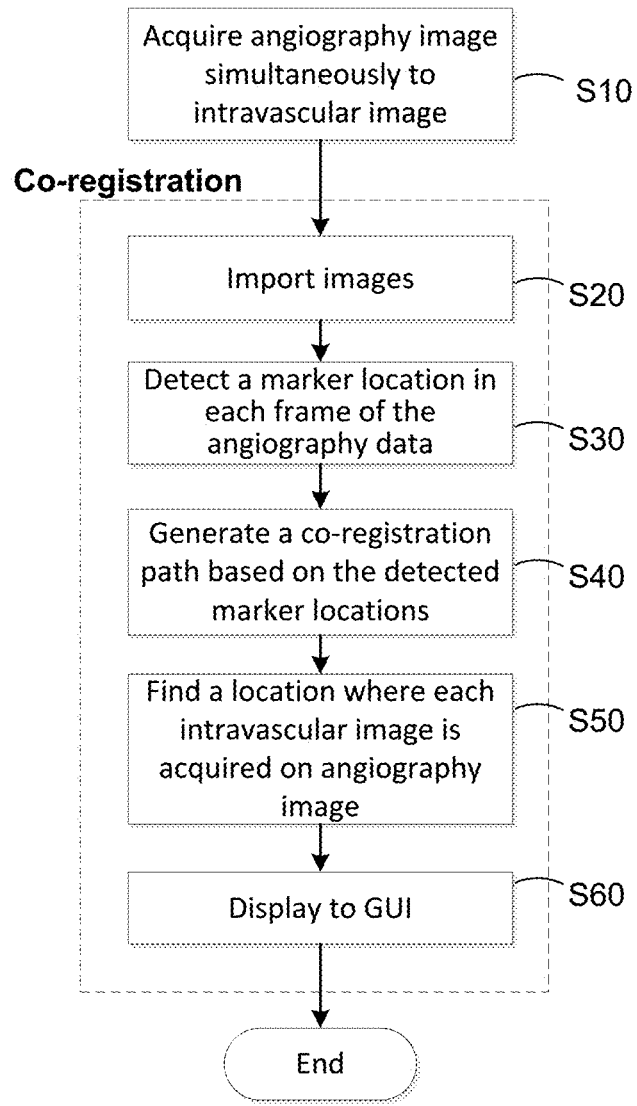
FIG. 2 is a flowchart illustrating various image processing steps in accordance with one or more aspects of the present disclosure.

Referring now to FIG. 2, a flowchart illustrating various steps for co-registering angiography data obtained from the angiography system 20 with intravascular imaging data obtained from the intravascular imaging system 30. The following steps for co-registration of angiography data with intravascular image data is applicable for a directly detected imaging catheter path as well as an imaging catheter path created as a regression line based on directly detected radiopaque marker locations based upon a regression line that is calculated. In the first step S10, angiography data such as angiography image frames are acquired simultaneous to the acquisition of intravascular image frames. Then, in step S20, the process for co-registration is initiated with importing both the angiography image frames and the intravascular image frames to an image processor. Subsequently, in step S30, a radiopaque marker location is detected for each angiography image frame from the angiography data. Each angiography image frame from the acquired angiography data may include a dark point that corresponds to the radiopaque marker of the catheter 38. The dark point that corresponds to the radiopaque marker of the catheter 38 is recognized by the image processor. The image processor stores the location of the radiopaque marker for each frame from a plurality of angiography image frames in a storage database.

In step S40, a co-registration path based on the detected radiopaque marker locations is generated. The co-registration path may represent the area where the image pullback is performed. The co-registration path may also represent a targeted region of a patient's coronary artery. The co-registration path may be generated for an entire angiography image frame or for selected one or multiple angiography image frames.

In step S50, a location where each intravascular image frame is acquired with respect to the angiography image frame is determined. In particular, a location is determined where each intravascular image is acquired in the global view of a coronary artery tree is searched using the information of the location of the detected radiopaque marker and the generated co-registration path. In step S60, the location where each intravascular image is acquired in the global view of the coronary artery tree is displayed on the angiography image frame within a GUI. The angiography image frame may also be displayed with an intravascular image frame. Each acquired intravascular image frame has an acquisition location, and it is visually represented on the displayed angiography image with the generated co-registration path. If a user prefers, the co-registration path can be selected not to overlay on the displayed angiography frame. After displaying within a GUI, the process for co-registering the angiography image frames and the intravascular image frames ends.

Figure 3:
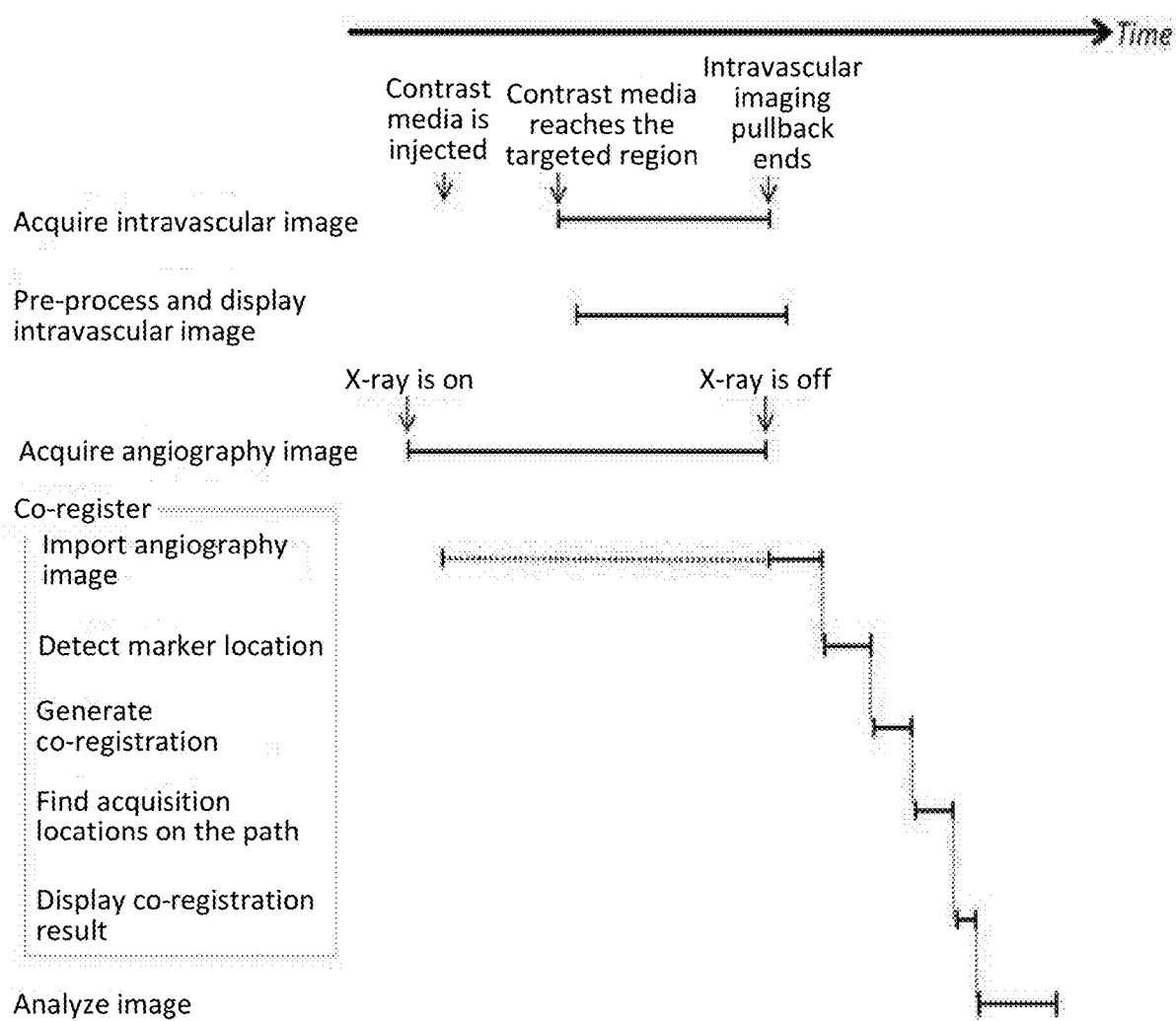
FIG. 3 is a time chart diagram illustrating a timing of a co-registration workflow in accordance with one or more aspects of the present disclosure.

Referring now to FIG. 3, a time chart illustrating at what point in time various steps associated with the co-registration process occur. Before referring to the various steps associated with the co-registration process, there are three events to note within the time chart. The first event corresponds to contrast media being injected into a patient's artery or blood vessel to clear the blood within the area where the intravascular image will be acquired. The contrast media may refer to a dye that is injected into the patient. Sometime after the contrast media is injected into the patient, the contrast media reaches the targeted region which corresponds to the second event along the time chart. A third event associated with the time chart includes the completion of an intravascular imaging pullback procedure which occurs after the contrast media reaches the targeted region of the patient.

The intravascular image frames are acquired when the contrast media reaches the targeted region of the patient and until the intravascular imaging pullback procedure is completed. Pre-processing and display of an intravascular image may occur in parallel to acquisition of the intravascular image frames with a certain time delay. The angiography data including angiography image frames are acquired when an X-ray is on until the X-ray is off. The acquisition of the angiography image frames may start before the contrast media reaches the targeted region of the patient. It is only necessary to acquire the angiography data until the third event where the intravascular imaging pullback procedure is completed. After the angiography data is acquired, the co-registration process may be initiated by importing the angiography data. The importing of the angiography data may occur after the intravascular imaging pullback procedure is completed.

The next step in the co-registration process includes detecting radiopaque marker locations for each angiography image frame. The detection of the radiopaque marker locations may occur after the angiography data is imported. Next, the co-registration path is generated after the radiopaque marker locations are detected for the angiography data. After generating the co-registration path the image processor may determine the acquisition locations of the intravascular image frames with respect to the co-registration path and the detected radiopaque marker location. Then, the angiography image frame and the intravascular image frame may be displayed on the monitor with overlaying the co-registration path and an artificial indicator representative of the acquisition locations of the intravascular image frames on the displayed angiography image frame. The displayed angiography image frame and intravascular image frame may be changed within the acquired angiography data and the intravascular data, along with the overlaying co-registration path and co-registration location. Both the angiography image frame and the intravascular image frame may appear as video that plays on the GUI. The displayed co-registration result is then analyzed by an interventional cardiologist by way of example.

Since the frame rate of intravascular image data is higher than that of the angiography image data, there are multiple intravascular frames of which acquisition location cannot be determined directly from the angiography image data by directly detecting radiopaque marker locations. Therefore, generation of a co-registration path is required to determine the acquisition locations for the intravascular image frames that do not have the corresponding angiography image frame.

Figure 4A:
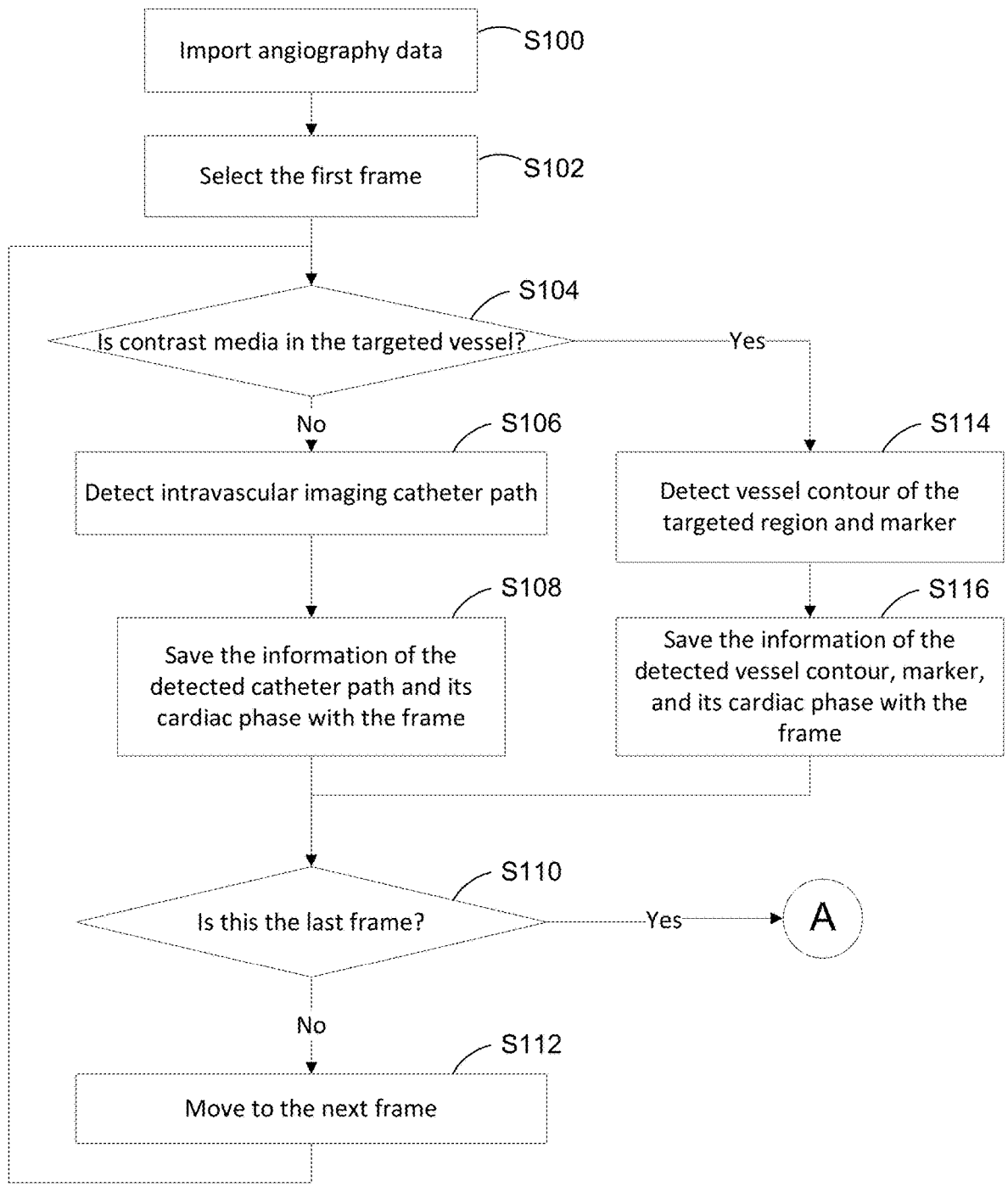
FIGS. 4A and 4B are flowcharts illustrating various steps for co-registration using a directly detected imaging catheter path in accordance with one or more aspects of the present disclosure.

Referring now to FIG. 4A, a flowchart illustrating various steps for generating a co-registration path based on an imaging catheter path that is directly detected. Since an imaging catheter path is used as the co-registration path, the accuracy of co-registration depends on the accuracy of the imaging catheter path generation. The advantage of using a directly detected imaging catheter path is that typically it is more accurate than other methods.

As an example, a guidewire over which the imaging catheter is delivered to the targeted vessel or a drive-cable of the imaging catheter can be used as the imaging catheter path. The imaging catheter path and the vessel contours can be detected by applying an edge detection filter, such as Sobel, Canny, Prewitt, Roberts, or others, and/or any combination from the edge detection filters. The radiopaque marker can be detected with, for example, Viterbi-based method or any edge detection method. The detected information is saved to each angiography image frame with the cardiac phase information if the corresponding ECG data is available. The cardiac phase information is obtained based on an ECG signal. One way to evaluate the cardiac phase information is calculating the percentage of cardiac cycle length as shown in FIG. 8.

Figure 8:
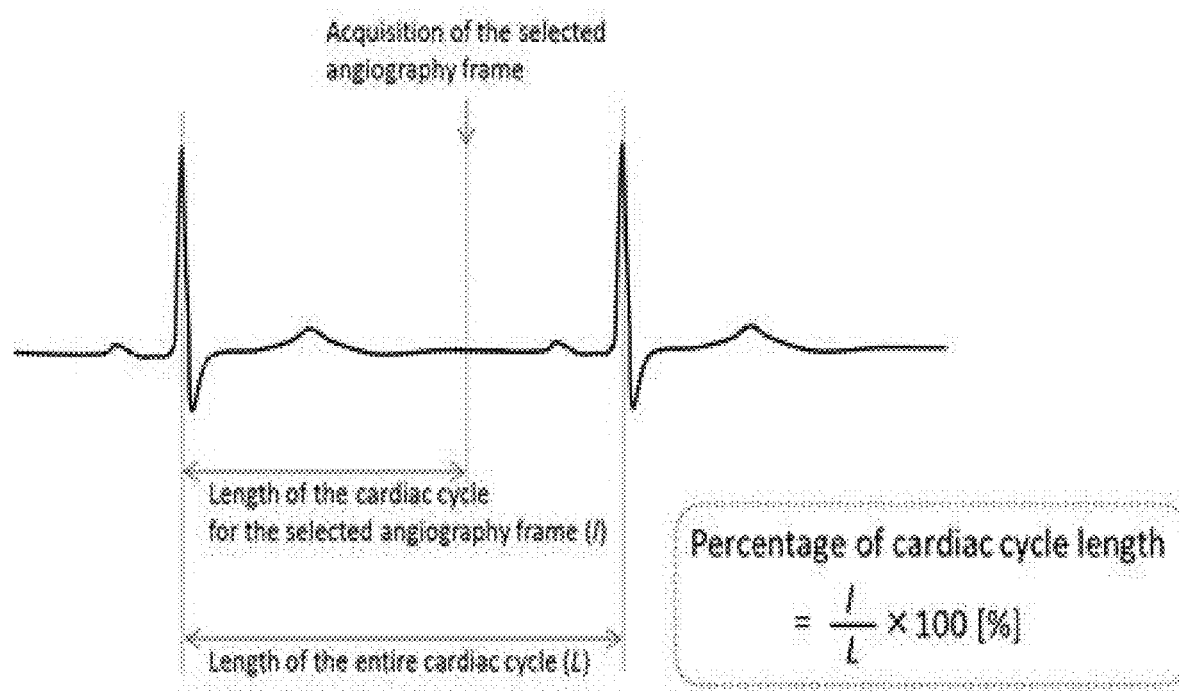
FIG. 8 is a diagram illustrating one example method of how to evaluate cardiac phase information in accordance with one or more aspects of the present disclosure.

In FIG. 8, cardiac phase information is evaluated based on the length of the entire cardiac cycle (L). The system may determine where along L a selected angiography image frame is acquired to determine the length of the cardiac cycle for the selected angiography image frame (I). To determine the percentage of cardiac cycle length with respect to the selected angiography image frame the following equation is applied: $((I/L)*100)$=percentage of cardiac cycle length.

In step S100, the process is initiated with the importing of angiography data including angiography image frames. The angiography data may also include cardiac phase information from the ECG 60 of FIG. 1. In particular each angiography image frame may include a cardiac phase signal value associated therewith according to time when the angiography image frame was acquired.

Figure 4B:
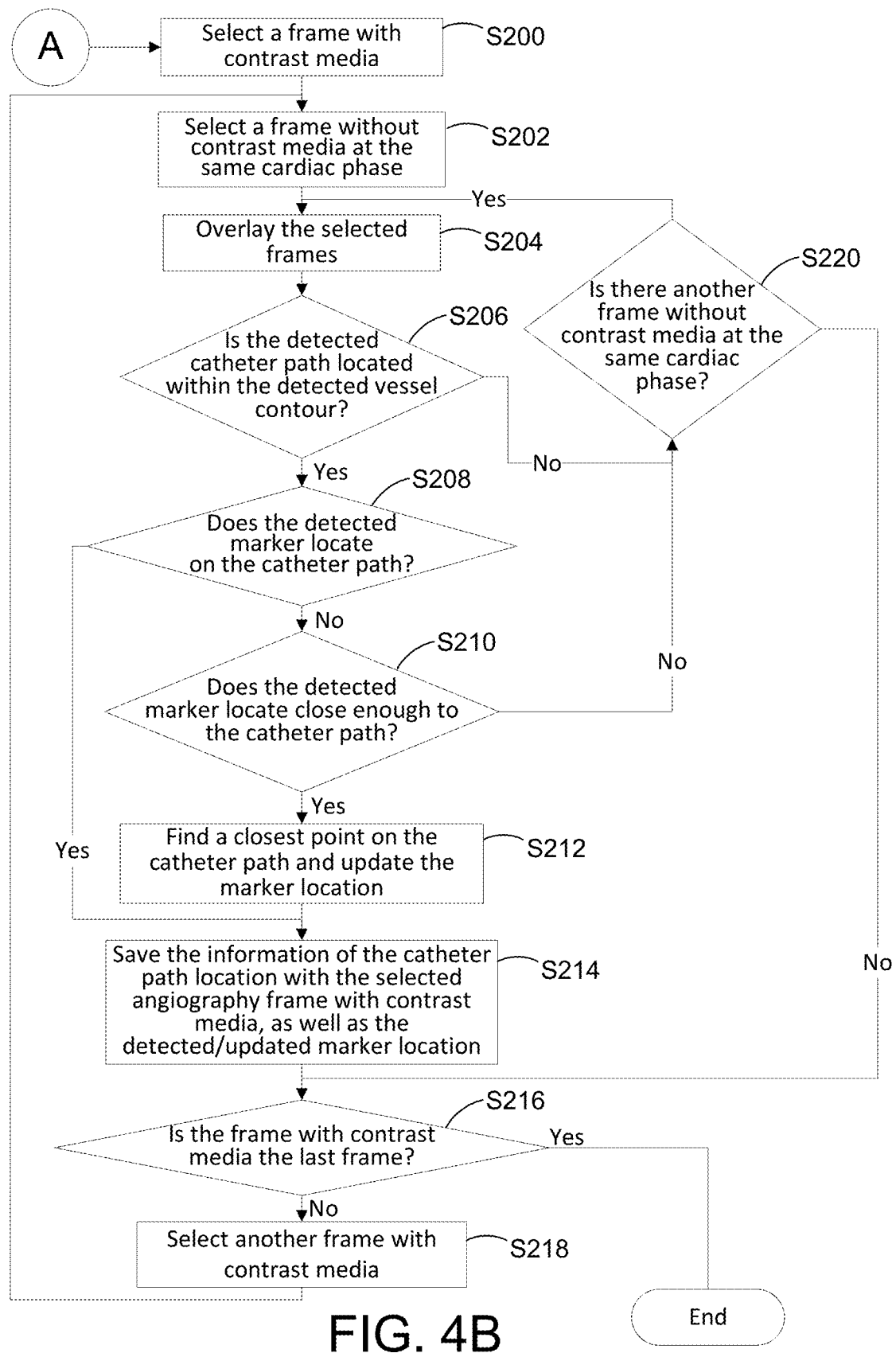

FIGS. 4A and 4B illustrate a case where the angiography image frames include the cardiac phase information (i.e., the angiography data are synchronized with the ECG signal) and there are enough angiography image frames without the contrast media in the targeted region of the blood vessel. In this case, the system can directly detect a co-registration path (i.e., an imaging catheter path). The accuracy of the imaging catheter path may be improved by the cardiac motion with the usage of the cardiac phase information and by checking the detected imaging catheter path location with detected radiopaque marker locations.

In step S102 a first angiography image frame is selected. In step S104, a determination is made with respect to whether there is contrast media in the targeted region of the blood vessel. To generate a directly detected imaging catheter path there are two requirements. The first requirement is including cardiac phase information associated with each angiography image frame. Cardiac phase information refers to an ECG signal synchronized with the angiography data. The second requirement includes a minimum quantity of angiography image frames that do not include contrast media in the targeted region of the blood vessel of a patient. Thus, in step S104 the determination of contrast media in the targeted region of the blood vessel divides the angiography image frames into two groups. One group of angiography image frames includes contrast media in the targeted region and another group of angiography image frames do not include contrast media in the targeted region. If there are not enough angiography image frames without the contrast media, then the imaging catheter path is determined using a regression line described below with respect to FIGS. 6A and 6B. The determination may be made based upon a predetermined threshold for angiography image frames without contrast media in the targeted region. The predetermined threshold may be automatically selected or inputted by a user of the imaging system 10 of FIG. 1.

The imaging system checks whether the imported angiography data has enough angiography image frames without the contrast media in the targeted blood vessel (i.e., the vessel region where the intravascular image is acquired). The imaging system may determine that the number of frames is sufficient if the angiography image frames without the contrast media are available for at least one cardiac cycle.

If it is determined in step S104 that the contrast media is not in the targeted region of the blood vessel, the first angiography image frame may be stored within the group of angiography image frames that do not include the contrast media in the targeted region and the process proceeds to step S106. In step S106, the imaging catheter path is detected for the first angiography image frame. In step S108, the information of the detected imaging catheter path and the cardiac phase associated with the first angiography image frame are saved with the first angiography image frame. After the detected imaging catheter path and the cardiac phase is saved with the first angiography image frame, it is determined whether the first angiography image frame is the last frame in step S110. In this example, the first angiography frame is not the last angiography image frame, the co-registration process proceeds to step S112 for selecting the next angiography image frame and the process returns to step S104. In this example, the next frame is the second angiography image frame and the steps are repeated until a last angiography image frame is selected.

Referring again to step S104 in FIG. 4A, if it is determined that there is contrast media in the targeted region of the blood vessel of the selected angiography image frame (Yes in step S104), the process proceeds to step S114. In step S114, the vessel contour of the targeted region and radiopaque marker are detected for the selected angiography image frame. Following step S114, the detected vessel contour, the detected radiopaque marker and the cardiac phase information associated with the selected angiography image frame are saved. Subsequently, it is determined in step S110 if the selected angiography image frame is the last frame. If it is determined that the selected angiography image frame is not the last frame (No in step S110), a next angiography image frame is selected in step S112 and the process returns to step S104.

In step S110, if it is determined that the selected angiography image frame is the last angiography image frame (Yes in step S110), the process proceeds to A which continues with the flowchart of FIG. 4B. Referring now to FIG. 4B, the flowchart illustrates various steps for determining whether the imaging catheter paths detected from one group of angiography image frames locate within the vessel contours detected from another group of angiography image frames in order to overlay the detected imaging catheter path onto the detected radiopaque marker.

In step S200, a first angiography image frame with contrast media is selected, and then in step S202 an angiography image frame without the contrast media that has the same cardiac phase as the first angiography image frame with contrast media is selected. In step S204, the two angiography images are overlaid. In step S206 it is determined whether the detected imaging catheter path is located within the detected vessel contour. If the detected imaging catheter path is located within the detected vessel contour (Yes in step S206), the process continues to step S208 to determine whether the detected radiopaque marker is located on the imaging catheter path. If it is determined in step S208 that the detected radiopaque marker is located on the imaging catheter path (Yes in step S208), the information of the imaging catheter path location is saved with the selected angiography image frame with the contrast media, as well as the detected radiopaque marker location in step S214. The process continues to step S216 where it is determined whether the selected first angiography image frame with the contrast media is the last angiography image frame with contrast media. If it is determined that the selected first angiography image frame with contrast media is not the last frame (No in step S216), then a next angiography image frame with contrast media is selected in step S218 and the process returns to step S202. Alternatively, if the selected angiography image frame with contrast media is the last frame (Yes in step S216), the process ends.

When it is determined in step S206 that the detected imaging catheter path is not located within the detected vessel contour (No in step S206), then it is determined whether there is another angiography image frame without contrast media at the same cardiac phase in step S220. If it is determined that there is another angiography image frame without contrast media at the same cardiac phase (Yes in step S220), then the process returns to step S204 and the new frame without contrast media at the same cardiac phase is overlaid with the selected angiography image frame with contrast media. Alternatively, if there is no angiography image frame without contrast media at the same cardiac phase (No in step S220), then the flowchart proceeds to step S216.

Returning to step S208, if it is determined that the detected radiopaque marker is not located on the imaging catheter path (No in step S208), it is then determined whether the detected radiopaque marker is located within a predetermined distance from the imaging catheter path in step S210. If the detected radiopaque marker is not within a predetermined distance of the imaging catheter path (No in step S210), the process returns to step S220. Alternatively, if the detected radiopaque marker is located within a predetermined distance from the imaging catheter path (Yes in step S210), then a closest point to the detected radiopaque marker on the imaging catheter path is updated as a marker location in step S212. Then in step S214, the updated marker location and the imaging catheter path location is saved with the selected angiography image frame with contrast media.

Figure 5:
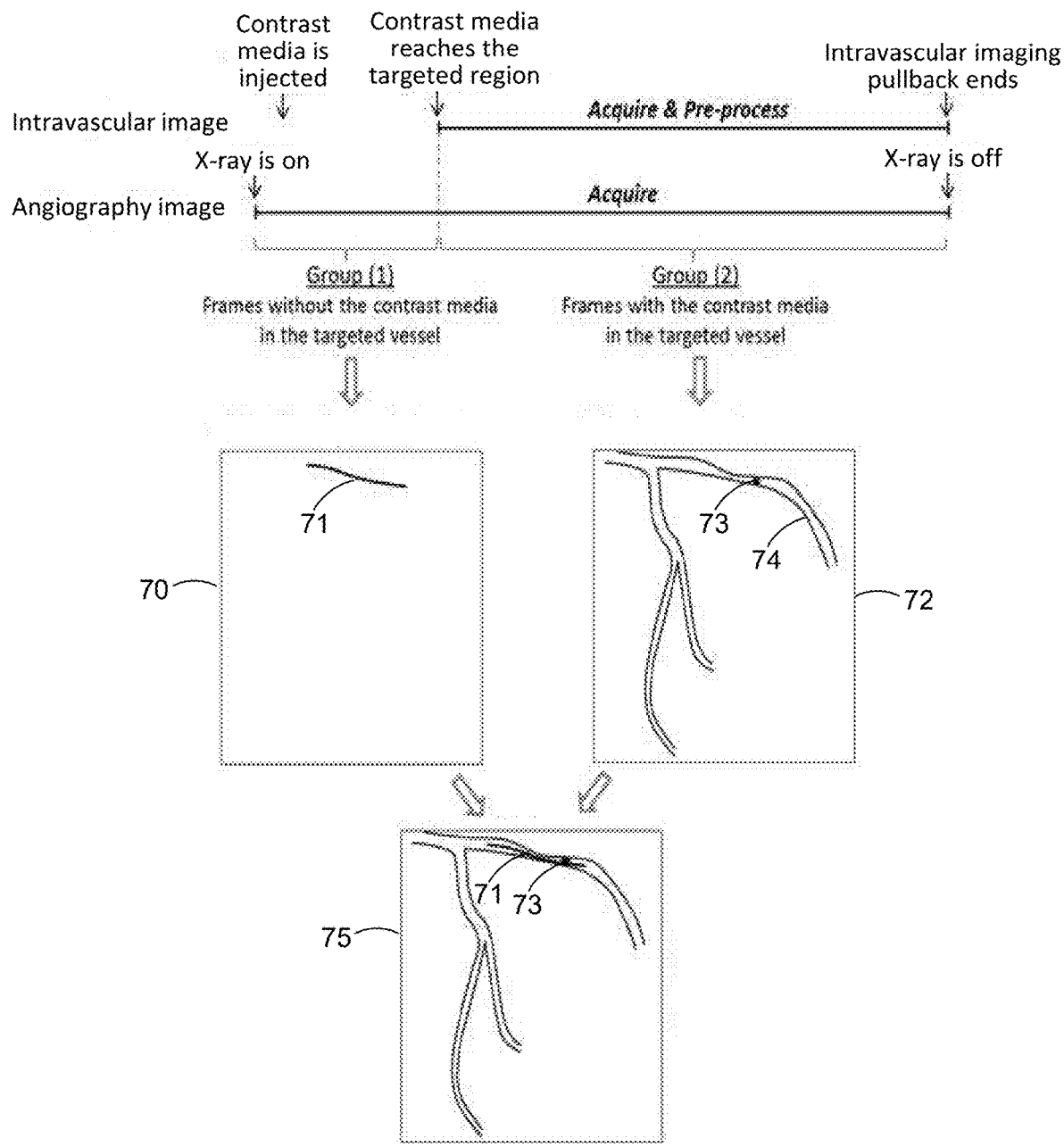
FIG. 5 is a visual representation of FIGS. 4A and 4B in accordance with one or more aspects of the present disclosure.

Referring now to FIG. 5 which illustrates the processes described in FIGS. 4A and 4B. The angiography data is acquired when an X-ray is on until the X-ray is off. The angiography data includes a plurality of angiography image frames which are divided into two different groups of angiography images frames. A first group of angiography image frames may include those angiography image frames without the contrast media in the targeted region of the targeted blood vessel. The first group of angiography image frames is acquired from the point where the X-ray is on until the contrast media reaches the targeted region. An image processor may be used to detect the imaging catheter path for the group of angiography image frames without the contrast media. The angiography image frame 70 includes an imaging catheter path 71 that is detected by the image processor.

The second group of angiography image frames may include angiography image frames with the contrast media in the targeted region of the targeted blood vessel. The angiography image frames with the contrast media are those angiography image frames that are acquired once the contrast media reaches the targeted region until the intravascular imaging pullback procedure is completed. The angiography image frame 72 includes the detected vessel contours 74 as well the detected radiopaque marker 73.

After the processes of detecting and saving for entire angiography image frames, the system chooses one angiography image frame from the group of angiography image frames with the contrast media and finds an angiography image frame with the same cardiac phase from the angiography image frames without the contrast media. Then, the imaging catheter path 71 detected from the selected angiography image frame 70 is overlaid on the selected angiography image frame 72 as shown in the angiography image frame 75 including the two overlaid angiography image frames (70, 72). The angiography image frame 75 is used to determine whether the detected imaging catheter path 71 is located within the detected vessel contours to make sure the detected imaging catheter path can be a representative line of the vessel's longitudinal direction. The angiography image frame 75 is also used to determine whether the detected radiopaque marker 73 is located on or within a certain distance from the detected imaging catheter path. Using the overlaid image 75, the system may determine whether the detected radiopaque marker is located on or within a certain distance from the detected imaging catheter path. The threshold of the distance can be predetermined by the system or determined by a user. If the overlaid image meets both criteria, the information of the detected imaging catheter path location is saved with the selected angiography frame with the contrast media. When the detected radiopaque marker is not located on the detected imaging catheter path but is located with a certain distance, the closest location to the detected radiopaque marker location on the imaging catheter path is searched, and its location is saved with the angiography frame with the contrast media by updating the detected marker location. If the overlaid image does not meet either one of the criteria, the system may search another angiography frame without the contrast media and follows the same process.

If there is no other angiography frame without the contrast media with the same cardiac phase, the system stops the process for the selected angiography frame with the contrast media. Then, the system selects another angiography image frame with the contrast media and repeats the entire process until the last frame with the contrast media is processed.

Figure 6A:
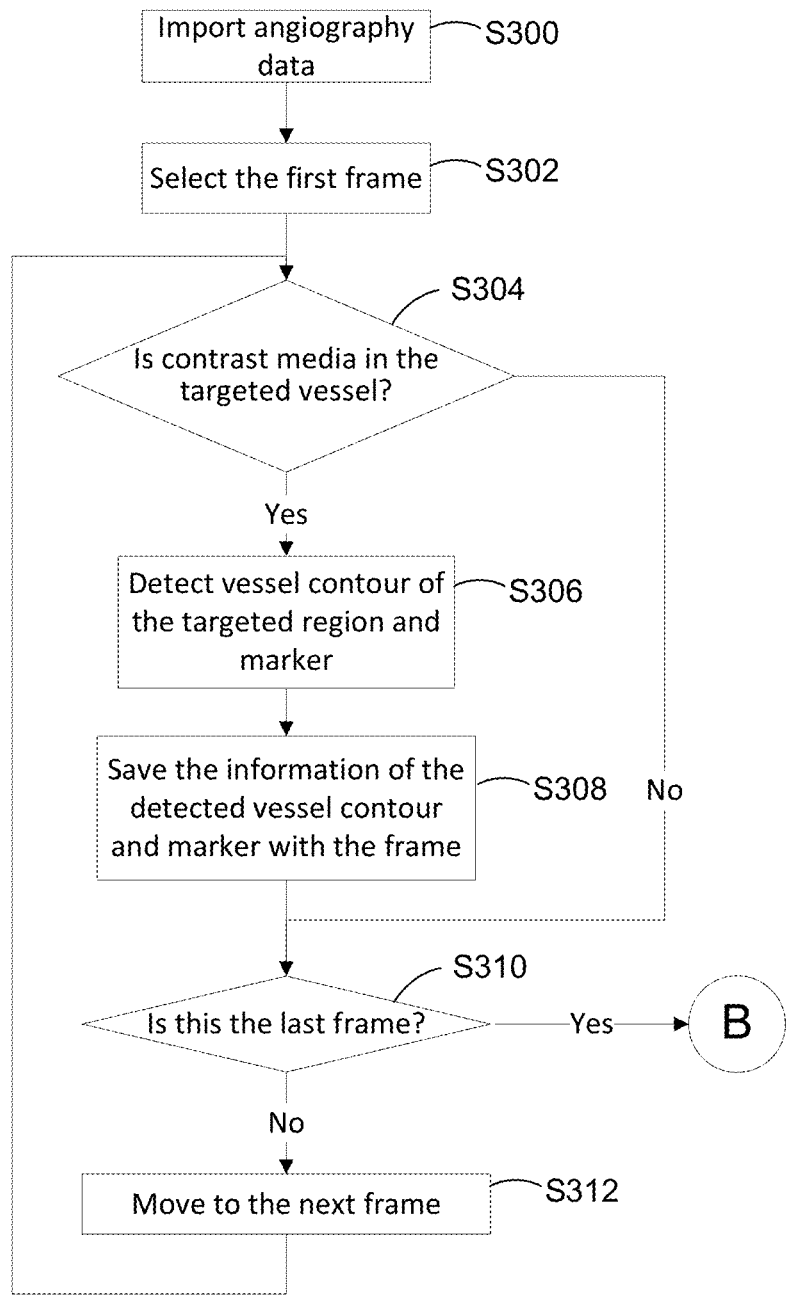
FIGS. 6A and 6B are flowcharts illustrating various steps for co-registration using an imaging catheter path based upon marker locations in accordance with one or more aspects of the present disclosure.
Figure 6B:
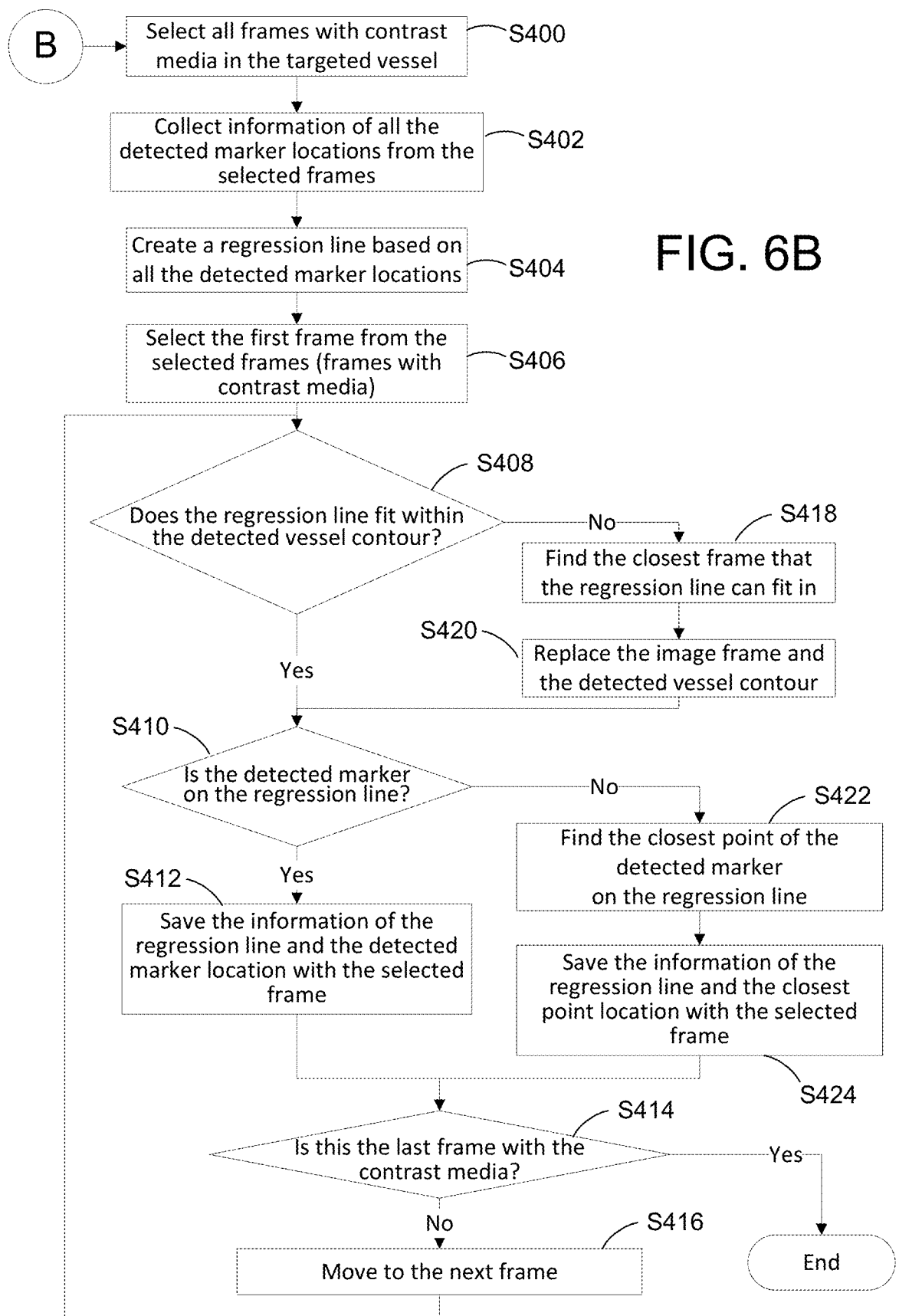

Referring now to FIGS. 6A and 6B, the flowcharts illustrate a case where the co-registration path is based on an imaging catheter path determined from a regression line that is based upon detected marker locations associated with the angiography data. The flowcharts of FIGS. 6A and 6B may be applied when the angiography data does include the cardiac phase information and/or when there are not enough angiography image frames without the contrast media in the targeted region of the blood vessel. In FIG. 6A, the process initiates with step S300 which includes importing angiography data that may include a plurality of angiography image frames. A first angiography image frame is selected in step S302. In step S304, it is determined whether contrast media is in the targeted region of the targeted blood vessel for the selected first angiography image frame. If it is determined that the contrast media is in the targeted vessel for the first angiography image frame (Yes in step S304), the vessel contour of the targeted region and the radiopaque marker are detected for the first angiography image frame selected in step S306. In step S308, the detected vessel contour and the radiopaque marker are saved with the first angiography image frame selected.

In step S310, it is determined where the selected angiography image frame is the last angiography image frame. If the selected angiography frame is not the last frame (No in step S310), then in step S312, the next angiography frame is selected. In this example, the second angiography image frame is selected in step S312 and the process returns to step S304 until every angiography image frame has been selected. Alternatively, if in step S310 it is determined that the last frame is selected (Yes in step S310), the process proceeds to B which continues with the flowchart of FIG. 6B. Returning to step S304, if the angiography image frame that is selected does not include contrast media (No in step S304), then the process skips ahead to step S310.

In FIG. 6B, the process is initiated by selecting all angiography image frames with contrast media in the targeted vessel in step S400. Next in step S402, all the detected radiopaque marker locations from the selected angiography image frames are collected. In step S404, a regression line is generated based on all the detected radiopaque marker locations collected from the selected angiography image frames using, for example, least squares regression method. In step S406, a first angiography image frame is selected from the angiography image frames with contrast media. In step S408, a determination is made with respect to whether the regression line fits within the detected vessel contour of the selected angiography image frame with contrast media. In the case where the regression line fits within the detected vessel contour (Yes in step S408), it is then determined whether the detected radiopaque marker is located on the generated regression line in step S410.

If the detected radiopaque marker is on the regression line (Yes in step S410), the information associated with the regression line and the detected radiopaque marker location is saved with the selected angiography image frame in step S412. In step S414 it is determined whether the selected angiography image frame is the last frame with contrast media. If the selected angiography image frame is the last frame (Yes in step S414), then the process for generating a co-registration path is concluded. Alternatively, if it is determined that the selected angiography image frame is not the last angiography image frame with contrast media (No in step S414), a next frame is selected in step S416 and the process returns to step S408.

Returning now to step S408, if it is determined that the regression line does not fit within the detected vessel contour (No in step S408), the closest angiography image frame that the regression line can fit within the detected vessel contour associated with the closest frame is determined in step S418. Then in step S420, the closest angiography frame along with the detected vessel contour replaces the selected angiography image frame.

In step S410, if the detected radiopaque marker is not located on the regression line (No in step S410), then a point on the regression line closest to the detected radiopaque marker is determined in step S422. Then the location of the closest point on the regression line that is associated with the selected angiography frame is saved in step S424.

Figure 7:
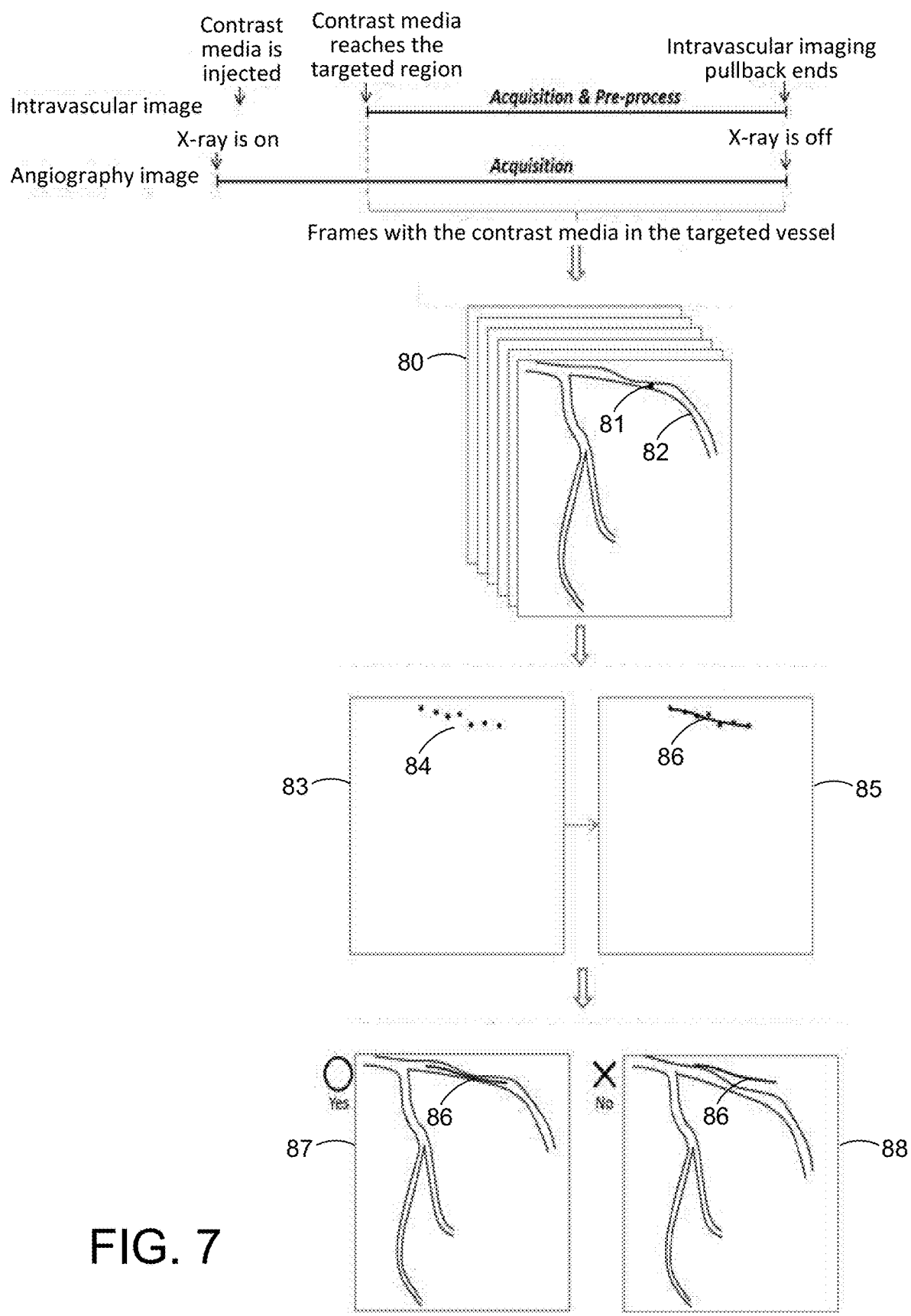
FIG. 7 is a visual representation of FIGS. 6A and 6B in accordance with one or more aspects of the present disclosure.

Referring now to FIG. 7, the angiography image frames 80 that include contrast media in the targeted region of a targeted blood vessel are grouped together. The angiography image frames 80 are the frames acquired once the contrast media reaches the targeted region until an intravascular imaging pullback procedure is completed. For each of the angiography image frames 80, an image processor may be used to detect the vessel contours 82 as well as the radiopaque marker 81. Then, all the information of the detected radiopaque marker locations 84 is collected and plotted in the same plane of the angiography image frame 83. Based on the detected radiopaque marker locations 84, a regression line 86 shown in the angiography image frame 85 is generated by using, for example, least squares regression method. After that, the system selects an angiography image frame from the previously selected angiography image frames and checks whether the regression line locates within the detected vessel contours. If the regression line 86 does not locate within the vessel contours as shown in the angiography image frame 88, the system searches another angiography image frame that the regression line 86 can locate within the vessel contours as shown in the angiography image frame 87 and that is acquired at the closest timing to the originally selected angiography image frame. The searched angiography image frame 87 with the closest timing replaces the originally selected angiography image frame. Upon replacement, the information of the detected vessel contours is also replaced, while the information of the detected radiopaque marker location is not replaced.

Then, the system checks whether the detected marker locates on the regression line. If the detected marker does not locate on the regression line, the system searches the closest location to the detected marker location on the regression line, and updates the information of the radiopaque marker location with the newly searched location. After that, the information of the detected or updated marker location and the regression line is saved with the selected angiography image frame. This process is repeated for each angiography image frame with the contrast media in the targeted region of the blood vessel. The process after generating a regression line can be performed in a different order. The system may first check whether the regression line locates within the detected vessel contours and update the angiography image frame if necessary for the group of angiography image frames with the contrast media. Then, the system can check whether the detected radiopaque marker locates on the regression line or not and updates its location if necessary.

Figure 9A:
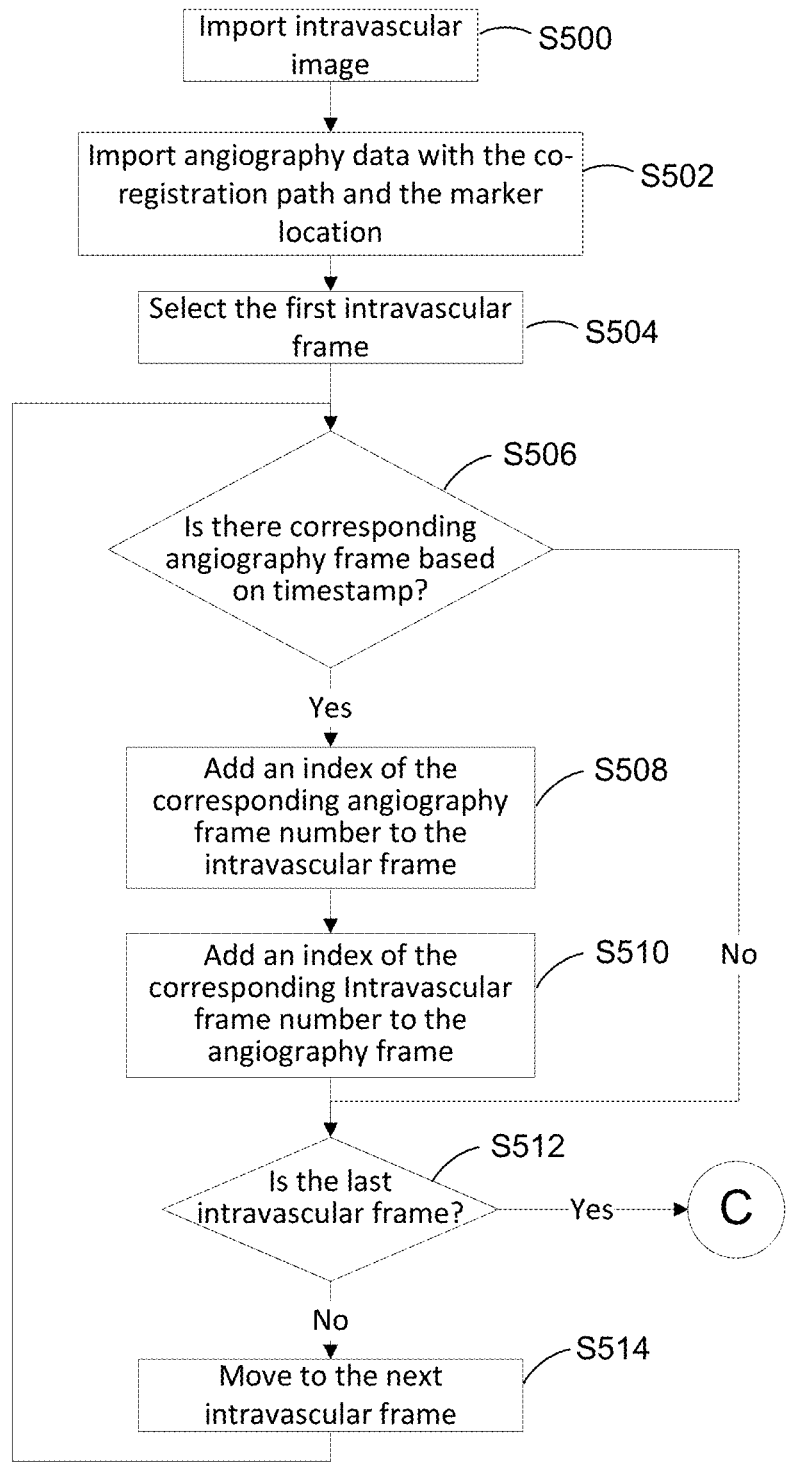
FIGS. 9A and 9B are flowcharts illustrating various steps for determining a location where acquired intravascular image frames are located on an angiography image frame in accordance with one or more aspects of the present disclosure.
Figure 9B:
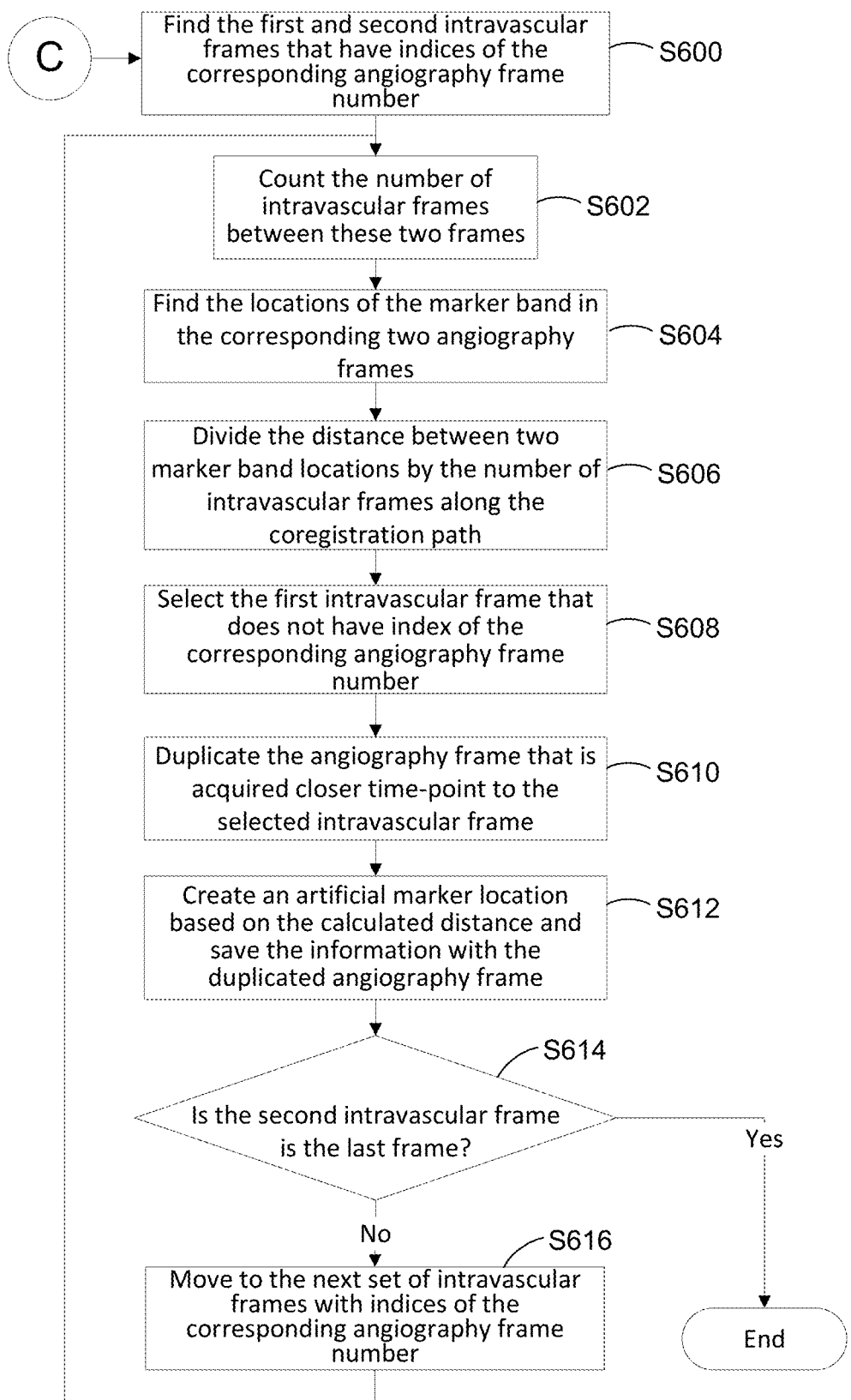

FIGS. 9A and 9B are flowcharts illustrating various steps to find an acquisition location of the intravascular image frame with respect to the angiography image frame. FIGS. 9A and 9B correspond to step S50 of FIG. 2. In step S500, the system imports intravascular image data including a plurality of intravascular image frames. In step S502, the angiography image frames with the co-registration paths and marker locations that were determined based on the co-registration steps outlined in FIGS. 4A & 4B or FIGS. 6A & 6B are imported. If the cardiac phase information was available as well as the requisite number of angiography image frames without contrast media, then the angiography image frames with the co-registration paths and marker locations that were determined based on the co-registration steps outlined in FIGS. 4A & 4B are imported. Alternatively, if the cardiac phase information was not available or there were not enough angiography image frames without the contrast media, then the angiography image frames with the co-registration paths and marker locations that were determined based on the co-registration steps outlined in FIGS. 6A & 6B are imported. In other words, the system includes the intravascular image frames and the angiography image frames with the co-registration path, either the directly detected imaging catheter path based on the steps outlined in the flowchart of FIGS. 4A & 4B or the newly generated imaging catheter path with the regression model, and the detected radiopaque marker locations based on the steps outlined in the flowchart of FIGS. 6A & 6B.

In step S504, a first intravascular image frame is selected. Next, in step S506 it is determined whether there is a corresponding angiography image frame based on the timestamp associated with the selected intravascular image frame. Initially the system may search the intravascular image frames that have the angiography image frames obtained at about the same time using the timestamps of both the intravascular image frame and the angiography image frame. If it is determined that there is a corresponding angiography image frame based on the timestamp (Yes in step S506), then, indices of the corresponding angiography frame number are added to the selected intravascular image frame in step S508, while the indices of the corresponding intravascular frame number are added to the angiography image frame in step S510. Alternatively, if it is determined that there is no corresponding angiography image frame based on the timestamp (No in step S506), then it is determined whether the selected intravascular image frame is the last intravascular image frame in step S512. If the selected intravascular image frame is not the last intravascular image frame (No in step S512), then a next intravascular image frame is selected in step S514 and returns to step S506. This process may be repeated until a last intravascular image frame is selected. If in step S512, it is determined that the selected intravascular image frame is the last intravascular image frame (Yes in step S512), then the flowchart continues to C which continues with the flowchart illustrated in FIG. 9B.

Referring now to FIG. 9B, a first and second intravascular image frames that have indices of the corresponding angiography image frame number are determined in step S600. In step S602, a number of intravascular image frames between the first and the second intravascular image frames are determined. Then, the locations of the radiopaque marker bands in the corresponding two angiography image frames are determined in step S604. In step S606, the distance between the two radiopaque marker band locations are determined and then divided by the number of intravascular image frames along the co-registration path that were determined in step S602. In step S608, a first intravascular image frame that does not have the index of the corresponding angiography frame number is selected. Then an angiography image frame that is acquired at a close time-point to the intravascular image frame selected in step S608 is duplicated in step S610. In step S612, an artificial marker location is generated based on the calculated distance and the information is saved with the duplicated angiography image frame. In step S614, it is determined whether the second intravascular image frame from step S600 is the last intravascular image frame. If the second intravascular image frame is not the last intravascular image frame (No in step S614), then a next set of intravascular image frames with indices of the corresponding angiography image frame number are selected in step S616, and the process returns to step S600. Alternatively, if the second intravascular image frame is the last intravascular image frame (Yes in step S614), then the process for finding an acquisition location of the intravascular image frame with respect to the angiography image frame is completed.

Figure 10:
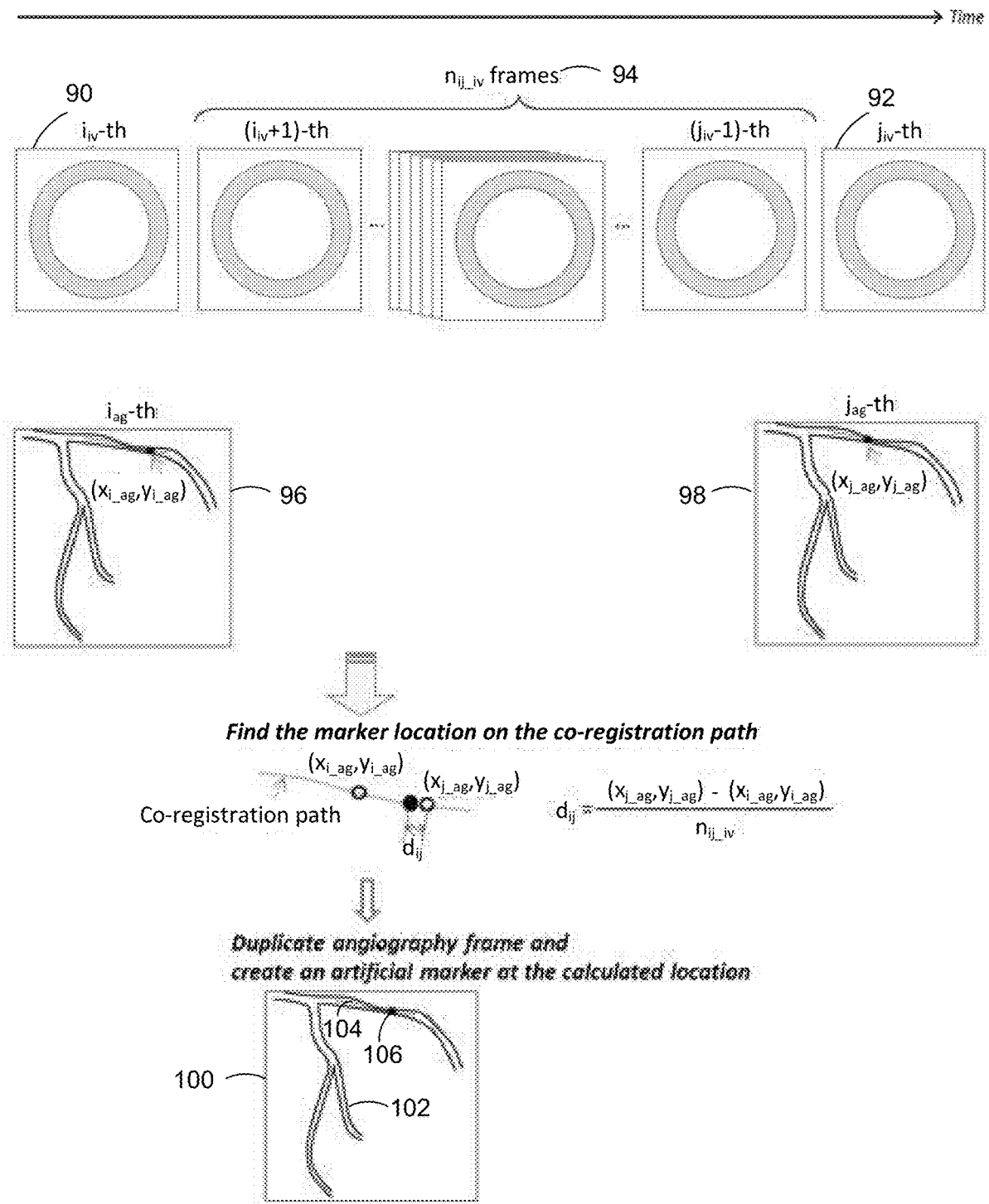
FIG. 10 is a diagram illustrating angiography image frames and intravascular image frames for determining a location of an acquired intravascular image frame on an angiography image frame in accordance with one or more aspects of the present disclosure.

Referring now to FIG. 10, the process outlined in the various steps of FIG. 9B are visually described. The system may find a first intravascular image frame 90 and a second intravascular image frame 92 [$i_{iv}$-th and $j_{iv}$-th frames] that have indices of the corresponding angiography image frame number, and counts the number of intravascular image frames between these two selected frames [$n_{ij\_iv}=j_{iv}-i_{iv}$] 94. The two corresponding angiography image frames are $i_{ag}$-th 96 and $j_{ag}$-th 98. Then, the system finds the corresponding radiopaque marker locations [$(x_{i\_ag}, y_{i\_ag})$ and $(x_{j\_ag}, y_{j\_ag})$] from the corresponding angiography image frames [$i_{ag}$-th and $j_{ag}$-th frame] (96, 98). Next, the system divides the distance between $(x_{i\_ag}, y_{i\_ag})$ and $(x_{j\_ag}, y_{j\_ag})$ by $n_{ij\_iv}$ along the co-registration path [$d_{ij}=\{(x_{j\_ag}, y_{j\_ag})-(x_{i\_ag}, y_{i\_ag})\}/n_{ij\_iv}$]. After that, the system selects the $(i_{iv}+1)$-th intravascular image frame and duplicates the angiography image frame 100 that is acquired at the closest timing on which the $(i_{iv}+1)$-th intravascular image frame is acquired.

When the angiography image frame 100 is duplicated, the imaging catheter path 104 is also duplicated. On the duplicated angiography image frame 100, the system generates a point 106 (i.e., an artificial marker) that locates at the calculated distance $d_{ij}$ from $(x_{i\_ag}, y_{i\_ag})$ along the co-registration path. The system then saves the artificial marker location on the duplicated angiography image frame 100 with the index of the corresponding intravascular image frame number. The system repeats these processes until it finishes them for $(j_{iv}-1)$-th intravascular image frame. Then, the system finds the second and the third intravascular image frames that have indices of the corresponding angiography image frame number, and repeats the above-described process. The process repeats until the system finishes with the second to last intravascular image frame and the last intravascular image frame that have the indices of the corresponding angiography frame number. The processes described above may be completed in a different order. The system can generate artificial markers every time it finds two intravascular image frames that have angiography image frames that are acquired at the same time.

In the method for generating a co-registration pair between the intravascular image frame and the angiography data, when $(i_{iv}+1)$-th intravascular image frame is selected, the angiography image frame is duplicated. However, in another method, the angiography image frame does not have to be duplicated. When $(i_{iv}+1)$-th intravascular image frame is selected, the angiography image frame that is acquired at the closest timing on which the $(i_{iv}+1)$-th intravascular image frame is acquired is searched, and its frame number is saved to the index of the $(i_{iv}+1)$-th intravascular image frame. Then, the acquisition location of the $(i_{iv}+1)$-th intravascular image frame is searched on the co-registration path using the same process described above. The searched location is saved to the $(i_{iv}+1)$-th intravascular image frame, along with the index of the angiography frame number.

Figure 11:
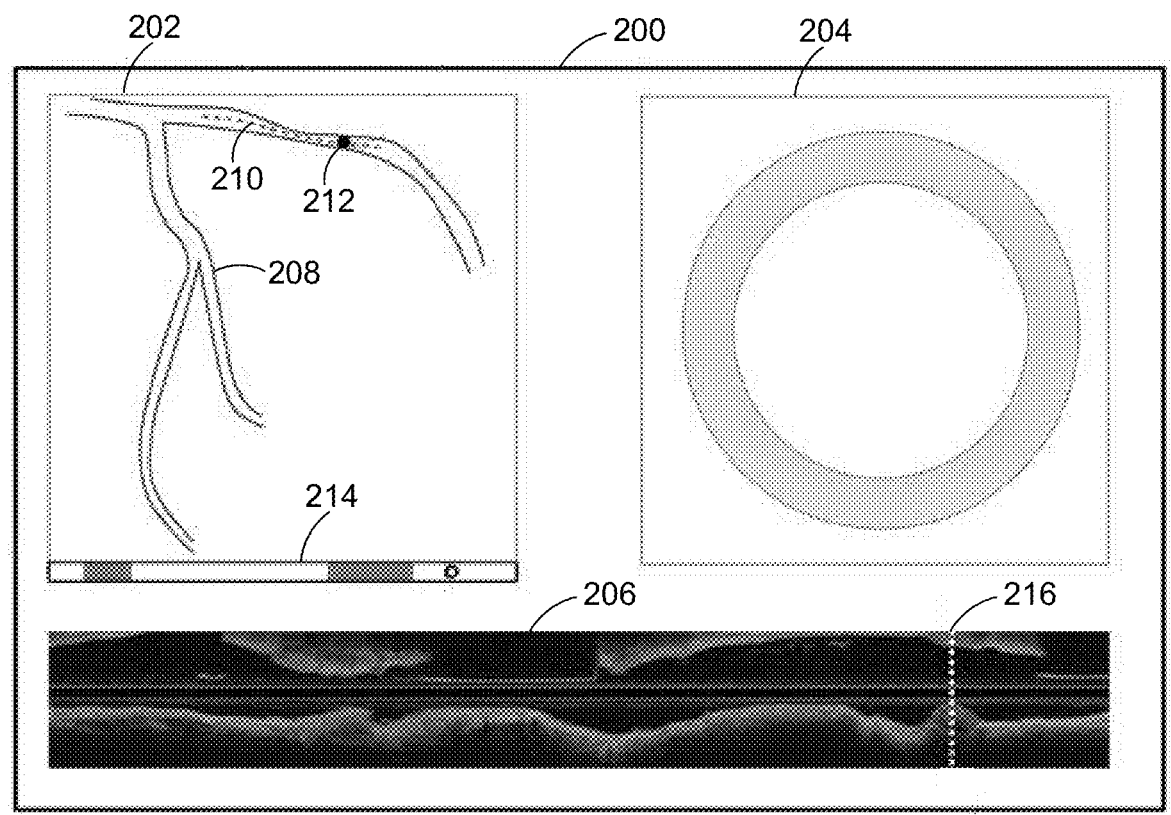
FIG. 11 is a diagram illustrating a graphical user interface for displaying a co-registration result in accordance with one or more aspects of the present disclosure.

Referring now to FIG. 11, the co-registration result may be displayed on a monitor or display using a graphical user interface (GUI) 200. The GUI may include the angiography image frame 202, the intravascular image frame 204 and a longitudinal view of a portion of the co-registration path 206. The co-registration path 210 is included in the angiography image frame 202 along with the vessel contours 208. The co-registration path 210 shows where the intravascular imaging pullback procedure was performed.

The system includes the intravascular image frame and the angiography image frame with the corresponding intravascular frame number. Once the intravascular image frame is selected by the system or by a user, the system searches the corresponding angiography frame using the indices of the angiography image frame and displays the angiography image frame on the monitor with an artificial indicator 212 overlaid on the angiography image frame. The artificial indicator 212 shows the position where the selected intravascular image frame 204 is acquired. The system also overlays the co-registration path 210 (i.e., the imaging catheter path that is directly detected or generated using a regression model) as its default setting, and a user can select not to display based on a user preference. In addition, the system displays the longitudinal view of the targeted vessel 206. The longitudinal view is generated using the acquired intravascular image frame, and may have multiple patterns. In one example, the longitudinal view shows the location where the intravascular image frame was acquired using an artificial indicator 216.

The system also has an ability to check the reliability of co-registration. The intravascular image frames that have indices of the corresponding angiography image frame are numbered as $j_{iv}$-th, $j_{iv}$-th, $k_{iv}$-th, $l_{iv}$-th, . . . , and $z_{iv}$-th. The system chooses two intravascular image frames that have the indices of the corresponding angiography image frame number [for example, $i_{iv}$-th and $k_{iv}$-th frames]. These two frames should be apart at least one frame that has the index of the corresponding angiography frame number [in this example, $j_{iv}$-th frame is skipped]. Then, the system estimates the co-registration location for each of the intravascular image frames that are acquired between the two selected frames, $i_{iv}$-th and $k_{iv}$-th frames. After that, the estimated co-registration location(s) is compared to the actual co-registration location(s) that is directly detected (and updated) from the corresponding angiography image frame [in this example, the comparison is performed for the $j_{iv}$-th frame]. The difference between the actual and the estimated locations is considered as reliability value. If the reliability value exceeds a certain threshold, an alert may be shown on the monitor when the co-registration result is displayed. The threshold can be predetermined by the system, or can be determined by a user based on a user preference. An alert can be a text message on the display, and/or a graphical output, such as a color-coded indicator 214 and an indicator with different line style or different shape.

In another embodiment of the present disclosure alternative methods are provided for imaging catheter path detection, step S106 in FIG. 4A, and for radiopaque marker detection, step S114 in FIG. 4A and step S306 in FIG. 6A.

First, a filter, e.g., homomorphic filter, is applied to reduce background noise that is created due to bone structure (e.g., ribs) and/or other organs (e.g., kidney). This process may be applied before step S104 in FIG. 4A or before step S304 in FIG. 6A.

Then, for step S106, i.e., the detection of imaging catheter path, an edge detection filter, such as Sobel, Canny, Prewitt, Roberts, or others, and/or any combination from the edge detection filters is applied, and the inner space of the dilated edges is filled. After that, a component(s) that contains the imaging catheter path is selected. The component selection can be done automatically by setting a pre-determined threshold or can be done semi-automatically by having one or multiple inputs from a user to specify the approximate location. Next, the selected component(s) is skeletonized. As a last step, the skeletonized result is smoothed by applying a smoothing function, for example, a cubic spline function or a polynomial fitting function.

For the detection of radiopaque marker, i.e., step S114 or step S306, after applying a filter to reduce the background noise, an edge detection filter, such as Sobel, Canny, Prewitt, Roberts, or others, and/or any combination from the edge detection filters is applied. Using the location information of the detected edge, the angiography image frame is masked to show only the area within the detected edges. Next, one or multiple dark points are searched in each masked angiography image frame. The number of points that are searched in each frame can be predetermined or can be set by a user, but it should be the same number throughout the angiography data.

After one or multiple dark points are searched in all the angiography image frames, the targeted radiopaque marker is determined for each frame. First, a user is asked to specify the approximate location of the radiopaque marker location in the first angiography image frame. Then, the targeted radiopaque marker is determined by searching the closest point from a point that a user inputs in the first angiography image frame. For the subsequent frames, the targeted radiopaque marker is determined by searching the closest point from the detected radiopaque marker location in the previous frame.

One or multiple dark points are searched and the determination of the targeted radiopaque marker can be done for each angiography image frame. In this case, the accuracy of radiopaque marker detection may be improved by narrowing down the searching area based on the targeted radiopaque marker location in the previous frame. Before searching one or multiple dark points, the angiography image frame is further masked to show only the area within the detected edges and proximal to the detected radiopaque marker location in the previous frame. A certain margin can be added to accommodate the movement of the targeted vessel due to cardiac motion. The margin can be predetermined by a system or can be set manually by a user.

A user input to specify the approximate location of the radiopaque marker location in the first angiography image frame can be obtained any time before the targeted radiopaque marker is determined in the first angiography image frame.

For the detection of the radiopaque marker, the determination of the targeted radiopaque marker can be achieved by tracking each searched point throughout the angiography data after one or multiple dark points are searched in all angiography image frames. Then, one or multiple dark points are searched in each angiography image frame. The number of points that are searched in each frame can be pre-determined or can be set by a user, but it should be the same number throughout the angiography data. Since only the radiopaque marker should move in one particular direction, i.e., the longitudinal direction of the targeted vessel, the targeted radiopaque marker can be determined by finding one point that moves in the particular direction. For tracking, a Viterbi-based method or a Speeded Up Robust Features (SURF) method may be used by way of example.

In another embodiment of the present disclosure, different co-registration options may be available in the case that the angiography image data is not available for an entire period of the intravascular imaging pullback. This situation may occur when a user turns off X-ray during the pullback accidentally or intentionally, and/or the system encounters any problem at step S20 in FIG. 2. When the angiography image data is not available for the entire period of the pullback, after a user selects to perform co-registration, the system asks a user whether the user would like to continue with the co-registration process. If the user selects to continue, the image processor checks the angiography image data and selects an option from two other options. The system selects Option A when the angiography image data is available partially during the pullback, and selects Option B when no angiography image data is available during the pullback. Option A is described with reference to FIGS. 12 and 13, and Option B is described with reference to FIG. 14 as described below. In other situations, some of the angiography image frames may not have the sufficient quality for the marker detection image processing or for co-registration processing purpose. In these situations, the system or the image processor 40 may determine whether there is a valid (available) angiography image frame, for co-registration, acquired during the pullback, and may use the marker location detected in the valid angiography image frame to calculate an acquisition location of at least one of the intravascular image frames. In this situation, the system selects Option A and using the valid angiography image frames as the available angiography image frames during the pullback. In a case where there is no valid angiography image frame acquired during the pullback, the system selects Option B.

Figure 12:
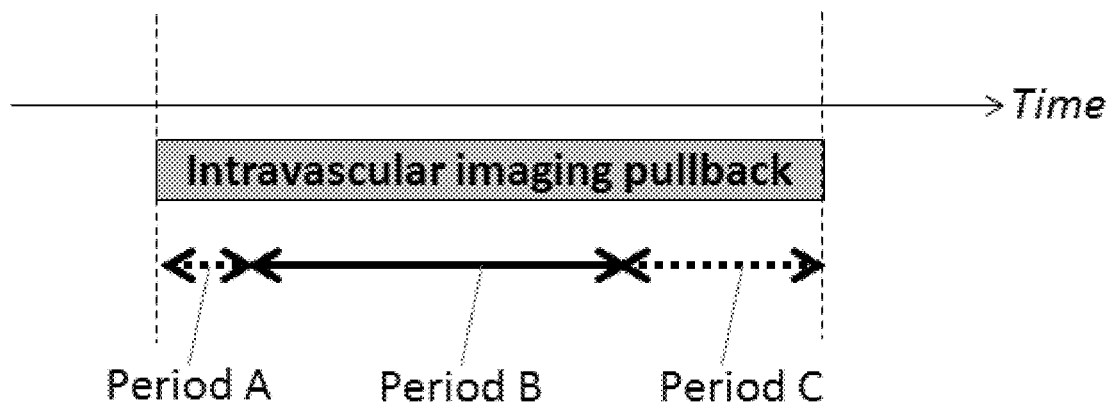
FIG. 12 is a diagram illustrating different periods during intravascular imaging pullback in accordance with one or more aspects of the present disclosure.
Figure 13:
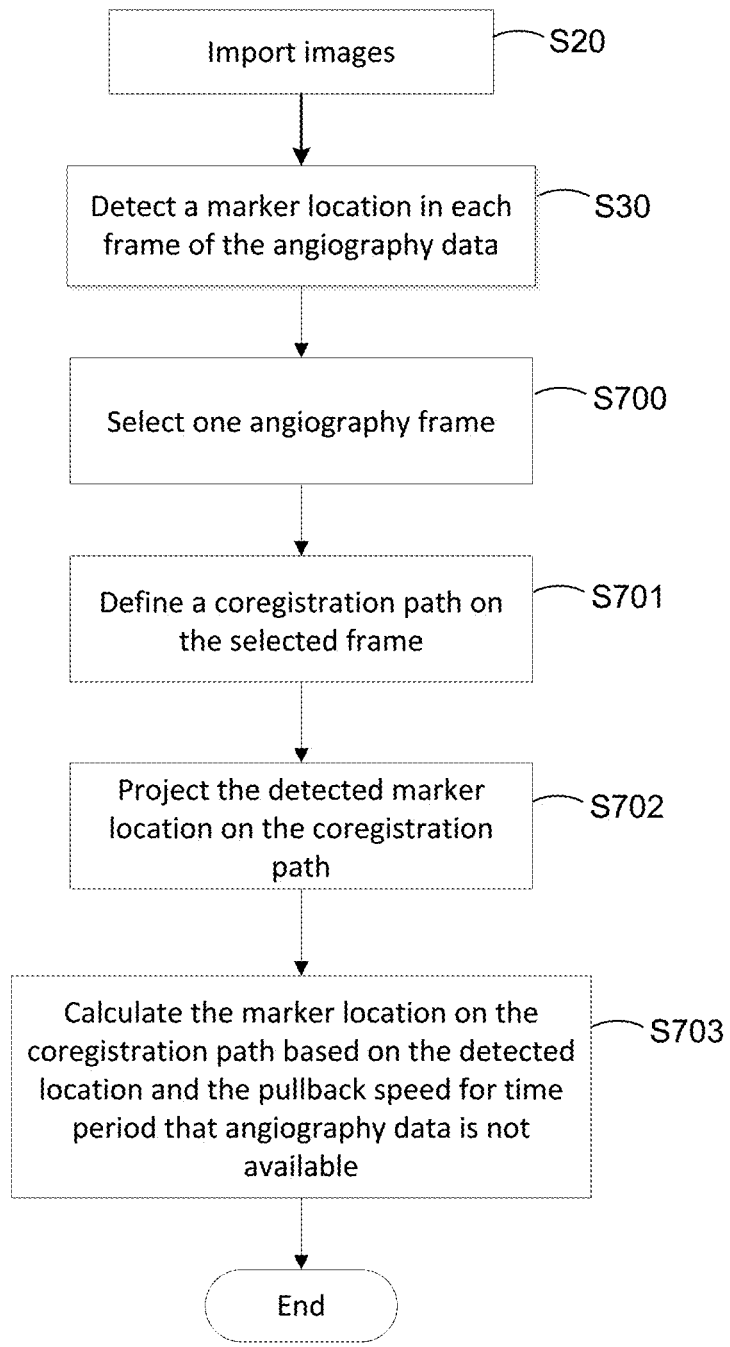
FIG. 13 is a flowchart illustrating various steps for calculating marker location on a co-registration path for a time period where angiography data is not available in accordance with one or more aspects of the present disclosure.
Figure 14:
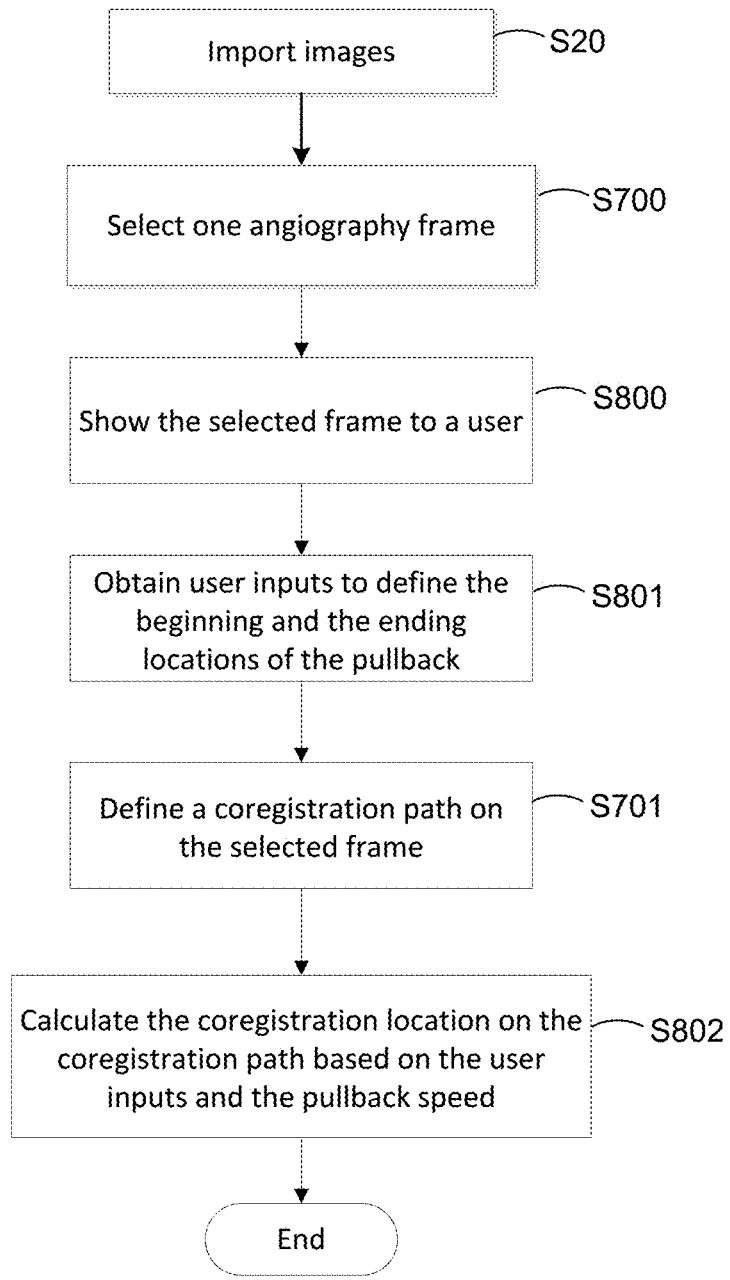
FIG. 14 is a flowchart illustrating various steps for calculating a co-registration location on a co-registration path in accordance with one or more aspects of the present disclosure.

FIG. 12 is a schematic figure describing when the angiography image is available relative to the intravascular imaging pullback. In this figure, period B is the time period when the angiography image is available, and periods A and C are the time periods when the angiography image is not available. For this Option A, steps S20-S40 in FIG. 2 may be changed to the steps that are described in FIG. 13, as one example method. FIG. 13 includes step S700 for selecting one angiography frame, then defining a co-registration path on the selected frame in step S701 in order to project the detected marker location on the co-registration path in step S702. In step S703, the marker location on the co-registration path is calculated based on the detected location and the pullback speed for the time period that angiography data is not available.

After importing the angiography data, first, the radiopaque marker is detected in the time period of the intravascular imaging pullback where the angiography image is available (period B in FIG. 12) in a similar manner to the case in which the angiography data is available for the entire pullback. Then, the system selects one angiography frame and defines a co-registration path. This path can be a vessel centerline or an imaging catheter path. Then, the detected radiopaque marker locations are projected onto the co-registration path. Based on the projected locations in the period where the angiography image was captured during a part of the intravascular imaging pullback, the radiopaque marker locations for time period(s) during the intravascular imaging pullback where the angiography image is not available (periods A and C in FIG. 12) are calculated along the extracted co-registration path using the pullback speed of the intravascular imaging. If the system calculates the acquisition locations of the intravascular image based on the detected radiopaque marker locations during the period where the angiography image was captured before a co-registration path is defined or before the locations are projected onto the path, the acquisition locations for the time period(s) where the angiography image was not captured can be calculated at a later time. For Option B, first, the system asks a user whether to capture a new angiography image. After the new angiography image is acquired and delivered to the image processor, the image processor will continue with the co-registration process. One example way of the co-registration process for this Option B, which corresponds to steps S20-S40 in FIG. 2, is described in FIG. 14. If the angiography data contains multiple frames, one angiography frame is selected first. This selection can be automatic by the system or selected manually by a user. Then, a user is requested to place inputs at the start and end locations of the intravascular imaging pullback on the selected frame. Subsequently, the system extracts a co-registration path in the selected frames and calculates the co-registration locations on the extracted path in the similar manner to Option A, during periods A and C. The extraction can be performed before the system obtains user inputs. Step S800 of FIG. 14 includes showing the selected frame to a user, then obtaining user inputs to define the beginning and the ending locations of the pullback. Step S802 includes calculating the co-registration location on the co-registration path based on the user inputs and the pullback speed.

Figure 15:
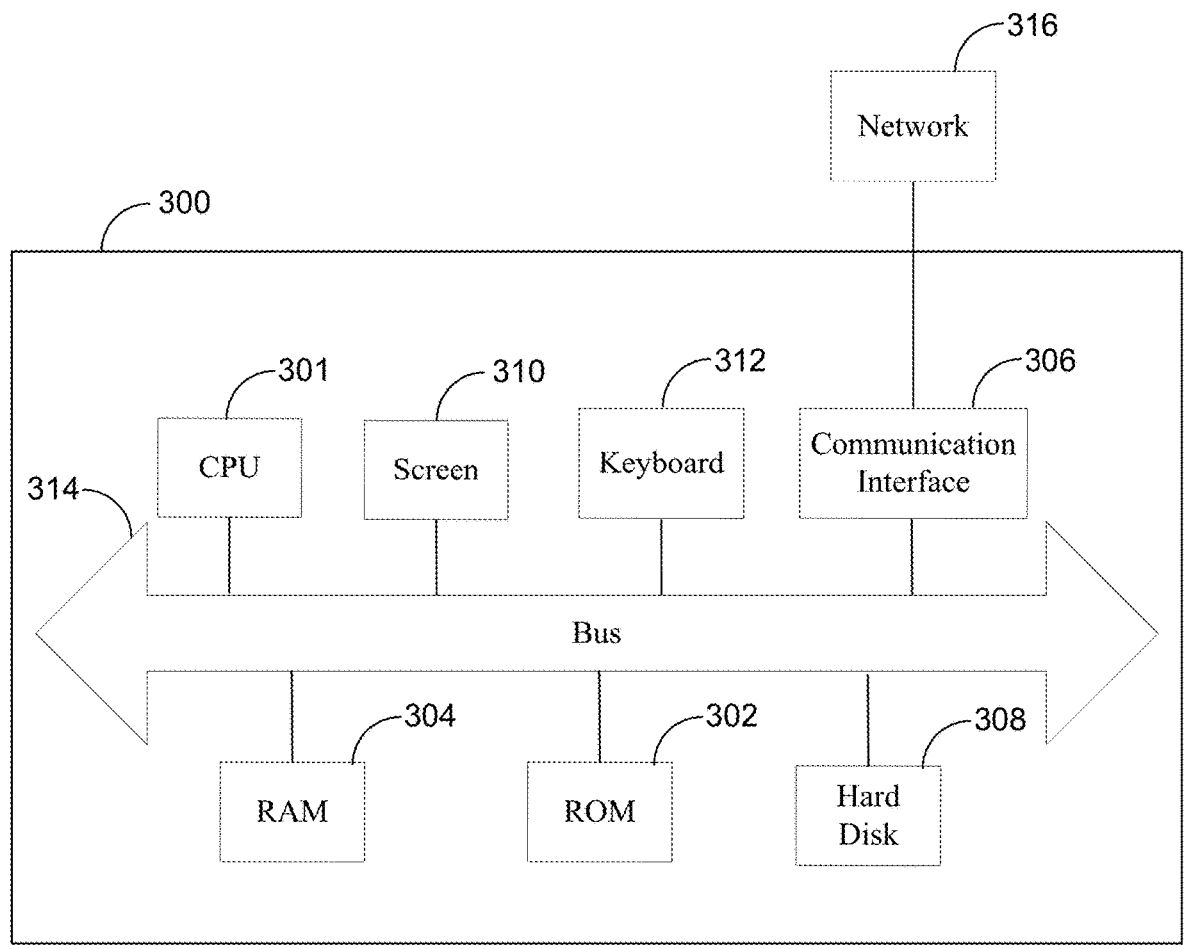
FIG. 15 shows a schematic diagram of an embodiment of a computer that may be used for generating a co-registration path in accordance with one or more aspects of the present disclosure.

FIG. 15 is an exemplary block diagram of a hardware configuration of the computer 34 of FIG. 1. However, the computer 300 may also be implemented in the angiography system 20 instead of the intravascular imaging system 30. In another embodiment of the present disclosure the computer 300 may be a stand-alone device encompassing the image processor 40 shown in FIG. 1.

The computer 300 include a central processing unit ("CPU") 301, a ROM 302, a RAM 304, a communication interface 306, a hard disk (and/or other storage device) 308, a display interface 310, a keyboard (or input interface; may also include a mouse or other input device in addition to the keyboard) 312 and a BUS or other connection lines (e.g., connection line 314) between one or more of the aforementioned components as shown in FIG. 15. The computer 300 may include one or more combinations of the other aforementioned components. The CPU 301 is configured to read and perform computer-executable instructions stored in a storage medium. The computer-executable instructions may include those for the performance of the methods and/or calculations described herein. The computer 300 may include one or more additional processors in addition to CPU 301, and such processors, including the CPU 301, may be used for acquiring information from an intravascular imaging system, an angiography system, and EGC device to determine a co-registration path with an indicator representative of a position along the co-registration path where an intravascular image frame is acquired. The computer 300 may further include one or more processors connected via a network connection (e.g., via network 316). The CPU 301 and any additional processor being used by the computer 300 may be located in the same telecom network or in different telecom networks.

The I/O or communication interface 306 provides communication interfaces to input and output devices, which may include the two light source 33, a communication cable and a network (either wired or wireless), a keyboard 312, a mouse, a touch screen or monitor 50.

Any methods and/or data of the present disclosure, such as the methods for generating a co-registration path, may be stored on a computer-readable storage medium. A computer-readable and/or writable storage medium used commonly, such as, but not limited to, one or more of a hard disk (e.g., the hard disk 308, a magnetic disk, etc.), a flash memory, a CD, an optical disc (e.g., a compact disc ("CD") a digital versatile disc ("DVD"), a Blu-Ray™ disc, etc.), a magneto-optical disk, a random-access memory ("RAM") (such as the RAM 304), a DRAM, a read only memory ("ROM"), a storage of distributed computing systems, a memory card, or the like (e.g., other semiconductor memory, such as, but not limited to, a non-volatile memory card, a solid state drive, SRAM, etc.), an optional combination thereof, a server/database, etc. may be used to cause a processor, such as, the processor or CPU 301 of the aforementioned computer 300 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

The above described devices, systems, and methods can be implemented by supplying one or more computer-readable media having stored therein computer-executable instructions for realizing the above described operations to one or more computer devices that are configured to read the computer-executable instructions and execute them. In this case, the system or devices perform the operations of the above-described embodiments when executing the computer-executable instructions. Also, an operating system on the one or more systems or devices may implement the operations of the above described embodiments. Thus, the computer-executable instructions or the one or more computer-readable media storing the computer-executable instructions or the one or more computer-readable media storing the computer-executable instructions thereon constitute an embodiment.

While the above disclosure describes certain illustrative embodiments, the present disclosure is not limited to the above-described embodiments, and the following claims include various modifications and equivalent arrangements within their scope.

What is claimed is:

1. A method for performing co-registration between angiography image data and intravascular image data, the method comprising:
   importing angiography data including a plurality of angiography image frames acquired during a pullback of an intravascular imaging catheter including a radiopaque marker, and importing intravascular imaging data including a plurality of intravascular image frames acquired simultaneously to the angiography data, wherein the angiography image frames include contrast media in a targeted region;
   detecting a marker for the angiography image frames including contrast media in the targeted region;
   generating a path based upon the detected marker from the angiography image frames including contrast media, the path being a regression line generated based upon the detected marker; and
   calculating an acquisition location of one or more of the intravascular image frames, in one or more of the angiography image frames, using the generated path,
   wherein the regression line is stored as a co-registration path on the one or more of the angiography image frames.

2. The method of claim 1, further comprising:
   selecting an angiography image frame from the angiography image frames including contrast media;
   determining whether the generated path fits within a vessel contour associated with the selected angiography image frame; and
   determining whether the marker associated with the selected angiography image frame is on the generated path in response to a determination that the generated path fits within the vessel contour associated with the selected angiography image frame.

3. The method of claim 2, wherein the determining steps are repeated for each angiography image frame from the angiography image frames including contrast media until a last angiography image frame from the angiography image frames including contrast media.

4. The method of claim 2, wherein, when it is determined in the first determining step that the generated path does not fit within the vessel contour associated with the selected angiography image frame, the method further comprises:
   selecting a closest angiography image frame to the selected angiography image frame in which the generated path fits within a vessel contour associated with the closest angiography image frame, and replacing the selected angiography image frame with the closest angiography image frame.

5. The method of claim 2, wherein, when it is determined in the second determining step that the marker associated with the selected angiography image frame is not on the generated path, then a location on the generated path that is closest to the marker associated with the selected angiography image frame is stored as a new marker associated with the selected angiography image frame.

6. The method of claim 1, further comprising:
   selecting an angiography image frame with the generated path;
   determining at least two intravascular image frames from the plurality of intravascular image frames that correspond to the selected angiography image frame based on a timestamp;
   calculating an intravascular image frame acquisition location on the generated path based on the at least two intravascular image frames; and
   displaying the angiography image frame with the generated path and an indicator representing the intravascular image frame acquisition location.

7. The method of claim 1, further comprising:
   determining if there is a valid angiography image frame, for co-registration, acquired during the pullback,
   wherein in the calculating step, an acquisition location of at least one of the intravascular image frames is calculated, based on the marker detected in the valid angiography image frame.

8. The method of claim 1, further comprising:
   in a case that there is no valid angiography image frame, during the importing step, importing a first angiography image frame, for co-registration, acquired during the pullback;
   receiving a first user input location for designating a start location of the pullback, and a second user input location for designating an end location of the pullback, wherein the first and the second user input location are in the first angiography image frame; and
   determining an acquisition location of at least one of the intravascular image frames, in the first angiography image frame, based on the first user input location and the second user input location.

9. A non-transitory computer-readable storage medium storing a computer-readable program for causing a computer to execute the method according to claim 1.

10. An imaging apparatus for processing angiography image data, the imaging apparatus comprising:
    one or more processors that operate to:
    import angiography data including a plurality of angiography image frames acquired during a pullback of an intravascular imaging catheter including a radiopaque marker, and import intravascular imaging data including a plurality of intravascular image frames acquired simultaneously to the angiography data, wherein the angiography image frames include contrast media in a targeted region;
    detect a marker for the angiography image frames including contrast media in the targeted region;
    generate a path based upon the detected marker from the angiography image frames including contrast media, the path being a regression line generated based upon the detected marker; and
    calculate an acquisition location of one or more of the intravascular image frames, in one or more of the angiography image frames, using the generated path,
    wherein the regression line is stored as a co-registration path on the one or more of the angiography image frames.

11. A system for processing angiography image data, the system comprising:
    an angiography imaging device for obtaining angiography data;
    an intravascular imaging device for obtaining intravascular imaging data simultaneous to the angiography data; and
    one or more processors that operate to:
    import angiography data including a plurality of angiography image frames acquired during a pullback of an intravascular imaging catheter including a radiopaque marker, and import intravascular imaging data including a plurality of intravascular image frames acquired simultaneously to the angiography data, wherein the angiography image frames include contrast media in a targeted region;

detect a marker for the angiography image frames including contrast media in the targeted region;

generate a path based upon the detected marker from the angiography image frames including contrast media, the path being a regression line generated based upon the detected marker; and calculate an acquisition location of one or more of the intravascular image frames, in one or more of the angiography image frames, using the generated path, wherein the regression line is stored as a co-registration path on the one or more of the angiography image frames.

12. A method for performing co-registration between angiography image data and intravascular image data, the method comprising:

importing angiography data including a plurality of angiography image frames acquired during a pullback of an intravascular imaging catheter including a radiopaque marker, and importing intravascular imaging data including a plurality of intravascular image frames acquired simultaneously to the angiography data, wherein the angiography image frames include contrast media in a targeted region;

detecting a marker for the angiography image frames including contrast media in the targeted region;

generating a path based upon the detected marker from the angiography image frames including contrast media;

calculating an acquisition location of one or more of the intravascular image frames, in one or more of the angiography image frames, using the generated path;

selecting an angiography image frame from the angiography image frames including contrast media;

determining whether the generated path fits within a vessel contour associated with the selected angiography image frame; and determining whether the marker associated with the selected angiography image frame is on the generated path in response to a determination that the generated path fits within the vessel contour associated with the selected angiography image frame.

13. The method of claim 12, wherein the determining steps are repeated for each angiography image frame from the angiography image frames including contrast media until a last angiography image frame from the angiography image frames including contrast media.

14. The method of claim 12, wherein, when it is determined in the first determining step that the generated path does not fit within the vessel contour associated with the selected angiography image frame, the method further comprises: selecting a closest angiography image frame to the selected angiography image frame in which the generated path fits within a vessel contour associated with the closest angiography image frame, and replacing the selected angiography image frame with the closest angiography image frame.

15. The method of claim 12, wherein, when it is determined in the second determining step that the marker associated with the selected angiography image frame is not on the generated path, then a location on the generated path that is closest to the marker associated with the selected angiography image frame is stored as a new marker associated with the selected angiography image frame.

16. A non-transitory computer-readable storage medium storing a computer-readable program for causing a computer to execute the method according to claim 12.

17. An imaging apparatus for processing angiography image data, the imaging apparatus comprising:

one or more processors that operate to:

import angiography data including a plurality of angiography image frames acquired during a pullback of an intravascular imaging catheter including a radiopaque marker, and import intravascular imaging data including a plurality of intravascular image frames acquired simultaneously to the angiography data, wherein the angiography image frames include contrast media in a targeted region;

detect a marker for the angiography image frames including contrast media in the targeted region;

generate a path based upon the detected marker from the angiography image frames including contrast media;

calculate an acquisition location of one or more of the intravascular image frames, in one or more of the angiography image frames, using the generated path;

select an angiography image frame from the angiography image frames including contrast media;

determine whether the generated path fits within a vessel contour associated with the selected angiography image frame; and determine whether the marker associated with the selected angiography image frame is on the generated path in response to a determination that the generated path fits within the vessel contour associated with the selected angiography image frame.

* * * * *